(12) United States Patent
Stegemann et al.

(10) Patent No.: US 8,634,911 B2
(45) Date of Patent: Jan. 21, 2014

(54) PACING INTERVAL DETERMINATION FOR VENTRICULAR DYSSYNCHRONY

(75) Inventors: Berthold Stegemann, Aachen (DE); Vinayakrishnan Rajan, Maastricht (NL); Michael P. Frenneaux, Kincardineshire (GB)

(73) Assignee: Medtronic, Inc., Minneapolis, MN (US)

( * ) Notice: Subject to any disclaimer, the term of this patent is extended or adjusted under 35 U.S.C. 154(b) by 369 days.

(21) Appl. No.: 12/916,033

(22) Filed: Oct. 29, 2010

(65) Prior Publication Data
US 2012/0109247 A1   May 3, 2012

(51) Int. Cl.
*A61N 1/37* (2006.01)

(52) U.S. Cl.
USPC ............................................................. 607/9

(58) Field of Classification Search
USPC .................................. 607/9, 17, 30
See application file for complete search history.

(56) References Cited

U.S. PATENT DOCUMENTS

| | | | |
|---|---|---|---|
| 5,713,930 A | 2/1998 | Van der Veen et al. | |
| 6,915,164 B2 | 7/2005 | Bradley et al. | |
| 7,139,610 B2 | 11/2006 | Ferek-Petric | |
| 7,203,542 B2 | 4/2007 | Obel | |
| 7,245,970 B2 | 7/2007 | Zhu et al. | |
| 7,711,420 B2 | 5/2010 | Baynham et al. | |
| 2003/0083700 A1 | 5/2003 | Hill | |
| 2004/0172079 A1 | 9/2004 | Chinchoy | |
| 2005/0038478 A1 | 2/2005 | Klepfer et al. | |
| 2007/0250125 A1* | 10/2007 | Lindh et al. | 607/9 |
| 2010/0114232 A1* | 5/2010 | Min | 607/28 |

FOREIGN PATENT DOCUMENTS

| | | |
|---|---|---|
| WO | 01/03769 | 1/2001 |
| WO | 2010019444 A1 | 2/2010 |
| WO | 2010042535 A2 | 4/2010 |

OTHER PUBLICATIONS (PCT/US2011/058248) PCT Notification of Transmittal of the International Search Report and the Written Opinion of the International Searching Authority.

\* cited by examiner

*Primary Examiner* — George Manuel
*Assistant Examiner* — Minh Duc Pham
(74) *Attorney, Agent, or Firm* — Reed A. Duthler

(57) ABSTRACT

A left-ventricular pacing interval and a right-ventricular pacing interval for timing the delivery of pacing pulses to a left ventricle and a right ventricle of a heart, respectively, may be based an intrinsic conduction time interval between at least one of an atrial sensing event or an atrial pacing event of an atrial chamber of a heart and a ventricular sensing event of a ventricular chamber of the heart. In some examples, the left-ventricular pacing interval is based on the time interval, where the left-ventricular pacing interval is less than the time interval. In some examples, the right-ventricular pacing interval is based on the time interval, where the right-ventricular pacing interval is greater than the left-ventricular pacing interval and less than the time interval.

31 Claims, 9 Drawing Sheets

PACING INTERVAL DETERMINATION FOR VENTRICULAR DYSSYNCHRONY

TECHNICAL FIELD

This disclosure relates implantable medical devices, and, more particularly, to cardiac therapy delivery by implantable medical devices.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device may sense intrinsic depolarizations of the heart, and control the delivery of therapeutic stimulation to the heart based on the sensing.

SUMMARY

In general, the disclosure is directed to delivering pacing pulses to left and right ventricles of a heart of a patient, and determining pacing intervals that may be used to deliver the pacing pulses to the left and right ventricles. In some examples, the pacing intervals are based on an intrinsic conduction time interval from an atrial sensing event or an atrial pacing event of an atrial chamber of the heart to a ventricular sensing event of a ventricle of the heart, where the intrinsic conduction time is determined during a cardiac cycle in which the ventricle is not paced. For example, a left-ventricular pacing interval and a right-ventricular pacing interval may each be determined based on the intrinsic conduction time interval, where the left-ventricular pacing interval and the right-ventricular pacing interval are different from each other and where each pacing interval is less than the intrinsic conduction time interval. In applications in which pacing pulses are delivered to a left ventricle and a right ventricle based on the determined left-ventricular and right-ventricular pacing intervals, the left ventricle and the right ventricle may dyssynchronously activate and contract.

In accordance with one example described herein, a method includes determining, with a processor, a time interval between at least one of an atrial sensing event or an atrial pacing event of an atrial chamber of a heart and a ventricular sensing event of a ventricular chamber of the heart, determining, with the processor, a left-ventricular pacing interval based on the time interval, where the left-ventricular pacing interval is less than the time interval, and determining, with the processor, a right-ventricular pacing interval based on the time interval, where the right-ventricular pacing interval is greater than the left-ventricular pacing interval and less than the time interval.

In another example, a system is described that includes a stimulation generator that is configured to deliver a left-ventricular pacing pulse to a left ventricular chamber of a heart, and to deliver a right-ventricular pacing pulse to a right ventricular chamber of the heart, and a processor that is configured to detect at least one of an atrial sensing event or an atrial pacing event of an atrial chamber of the heart. According to the example, the processor is configured to determine a time interval between at least one of the atrial sensing event or the atrial pacing event of the atrial chamber of the heart and a ventricular sensing event of the ventricular chamber of the heart during a first cardiac cycle, determine the left-ventricular pacing interval based on the time interval, where the left-ventricular pacing interval is less than the time interval, and determine the right-ventricular pacing interval based on the time interval, where the right-ventricular pacing interval is greater than the left-ventricular pacing interval and less than the time interval. In the example, the processor is also configured to control the stimulation generator to deliver the left-ventricular pacing pulse upon expiration of the left-ventricular pacing interval that begins at detection of at least one of the atrial sensing event or the atrial pacing event of the atrial chamber during a second cardiac cycle, and deliver the right-ventricular pacing pulse upon expiration of the right-ventricular pacing interval that begins at detection of at least one of the atrial sensing event or the atrial pacing event of the atrial chamber during the second cardiac cycle.

In another example, a system is described that includes means for determining a time interval between at least one of an atrial sensing event or an atrial pacing event of an atrial chamber of a heart and a ventricular sensing event of a ventricular chamber of the heart, means for determining a left-ventricular pacing interval based on the time interval, where the left-ventricular pacing interval is less than the time interval, and means for determining a right-ventricular pacing interval based on the time interval, where the right-ventricular pacing interval is greater than the left-ventricular pacing interval and less than the time interval.

In an additional example according to the disclosure, a computer-readable storage medium is described that includes instructions that cause a programmable processor to determine a time interval between at least one of an atrial sensing event or an atrial pacing event of an atrial chamber of a heart and a ventricular sensing event of a ventricular chamber of the heart, determine a left-ventricular pacing interval based on the time interval, where the left-ventricular pacing interval is less than the time interval, and determine a right-ventricular pacing interval based on the time interval, where the right-ventricular pacing interval is greater than the left-ventricular pacing interval and less than the time interval.

In another aspect, the disclosure is directed to an article of manufacture comprising a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages of will be apparent from the description and drawings, and from the claims.

DETAILED DESCRIPTION

Devices, systems, and techniques for delivering cardiac rhythm management therapy, such as pacing therapy, to a heart of a patient are described. In addition, devices, systems, and techniques for determining when to deliver pacing therapy to a left ventricle and a right ventricle of a heart are described. As described herein, the timing of the delivery of the pacing pulses may be based on a time interval between at least one of an atrial sensing event or an atrial pacing event ($A_{s/p}$) of an atrial chamber of the heart and a ventricular sensing event ($V_s$) of a ventricular chamber of the heart. The time interval may be determined without delivering pacing therapy to the left and right ventricles. That is, the time interval may be determined during a cardiac cycle in which no pacing therapy is delivered to the ventricles, and, in some examples, the time interval is indicative of the intrinsic conduction time of the heart. For example, the time interval between the atrial sensing event or the atrial pacing event ($A_{s/p}$) and the ventricular sensing event ($V_s$) may be determined while pacing therapy to the left and right ventricles is suspended. A left-ventricular pacing interval may be determined based on the time interval and may be less than the time interval. A right-ventricular pacing interval may also be determined based on the time interval and may be greater than the left-ventricular pacing interval but less than the time interval.

In some examples, such as in applications in which pacing pulses are delivered to the left and right ventricles upon expiration of the left-ventricular and right-ventricular pacing intervals, respectively, the left and right ventricles may be depolarized via the pacing pulses before the ventricles are depolarized via intrinsic conduction from the atrioventricular (AV) node. For example, the left ventricle may be depolarized before the right ventricle, and both ventricles may be depolarized via pacing pulses before the ventricles are depolarized via intrinsic conduction from the AV node. Such a pacing therapy may induce a phase shift between mechanical activation of the left ventricle and mechanical activation of the right ventricle. That is, the pacing therapy may induce a dyssynchrony between the two ventricular chambers of the heart. With some patients, such as some patients suffering from diastolic heart failure, the phase shift may allow the left and right heart ventricles to expand at different times during diastole. This may help minimize the extent to which or even prevent the left ventricle and right ventricle from competing for space within pericardium.

Figure 1:
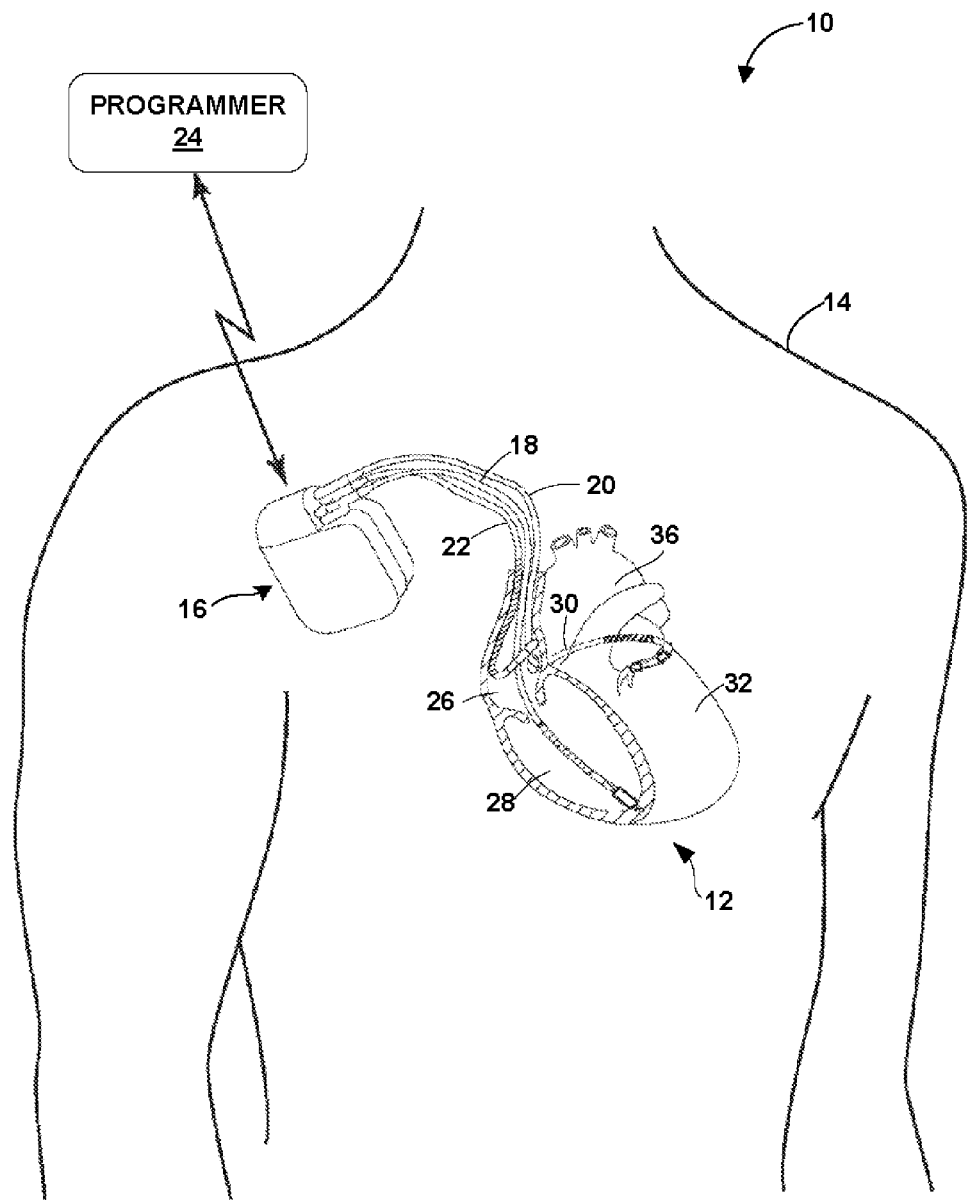
FIG. 1 is a conceptual diagram illustrating an example therapy system comprising an implantable medical device (IMD) that may be used to monitor one or more physiological parameters of a patient and/or provide therapy to the heart of a patient.

FIG. 1 is a conceptual diagram illustrating an example therapy system 10 that may be used to monitor and/or to provide therapy to heart 12 of patient 14. Therapy system 10 includes an implantable medical device (IMD) 16, which is coupled to leads 18, 20, and 22, and programmer 24. IMD 16 may be an implantable pacemaker that provides electrical signals to heart 12 and/or senses electrical activity of heart 12 via electrodes coupled to one or more of leads 18, 20, and 22. In some examples, IMD 16 may also include cardioversion and/or defibrillation functionalities.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12.

Right atrial (RA) lead 22 extends through one or more veins and the vena cava, and into the right atrium 26 of heart 12. In some examples, RA lead 22 is positioned in the inferior portion of right atrium 26. In some examples, RA lead 22 may be positioned in the posterior portion of right atrium 26 around the coronary sinus ostium, such as posteriorly to the coronary sinus ostium, and along the septum that separates right atrium 26 and left atrium 36. For example, RA lead 22 may be positioned such that RA lead 22 may sense electrical activity within right atrium 26 and/or pace right atrium 26.

In some examples, therapy system 10 includes one or more sensors (not shown in FIG. 1) adapted for sensing various hemodynamic conditions or other conditions of patient 14. For example, therapy system 10 may include one or more blood flow sensors, blood pressure sensors, tissue perfusion sensors, pulse oximeters, hematocrit sensors, patient activity sensors, or any other sensor adapted to sense one or more hemodynamic conditions or other conditions of patient 14. Depending on the configuration of therapy system 10, the one or more sensors may be internal or external to patient 14.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., outside the vasculature of patient 14), such as epicardial electrodes, external surface electrodes, subcutaneous electrodes, and the like. In some examples, as described in further detail below, IMD 16 provides pacing pulses to heart 12 based on the electrical signals sensed within heart 12. For example, IMD 16 may provide pacing pulses to right ventricle 28 and left ventricle 32 based on electrical signals sensed within right ventricle 28 and/or left ventricle 32, e.g., based on an intrinsic conduction time for electrical activity to traverse from right atrium 26 to right ventricle 28 and/or left ventricle 32 in the absence of pacing stimulation. The configurations of electrodes used by IMD 16 for sensing and pacing may be unipolar or bipolar.

IMD 16 may deliver a pacing pulse to left ventricle 32 via electrodes of LV lead 20, and IMD 16 may deliver a separate pacing pulse to right ventricle 28 via electrodes of RV lead 18. IMD 16 may also determine when to deliver the pacing pulses to left ventricle 32 and right ventricle 28, respectively. As described herein, IMD 16 may determine when to deliver pacing pulses to left ventricle 32 and right ventricle 28 so that each ventricle is depolarized by pacing from IMD 16 before the respective ventricle is intrinsically depolarized via conduction from the atrioventricular (AV) node and Purkinje system of heart 12. Such a pacing scheme may result in dyssnchronous activation and contraction of left ventricle 32 and right ventricle 28.

In one example, IMD 16 determines a left-ventricular pacing interval for pacing left ventricle 32 and a right-ventricular pacing interval for pacing right ventricle 28. The left-ventricular pacing interval may be a predetermined period of time between an atrial sense or pace event ($A_{s/p}$) and a time when IMD 16 delivers a pacing pulse to left ventricle 32 ($LV_P$). Thus, the left-ventricular pacing interval can also be referred to as an $A_{P/S}$-$LV_P$ interval or an $A_{P/S}$-$LV_P$ delay. By contrast, the right-ventricular pacing interval may be a predetermined period of time between an atrial sense or pace event ($A_{S/p}$) and a time when IMD 16 delivers a pacing pulse to right ventricle 28 ($RV_P$). Accordingly, the right-ventricular pacing interval may also be referred to as an $A_{P/S}$-$RV_P$ interval or an $A_{P/S}$-$RV_P$ delay.

In some examples, the left-ventricular pacing interval and the right ventricular pacing interval are each based on an intrinsic conduction time between an atrial chamber of heart 12 and a ventricular chamber of heart 12. As described in greater detail below with reference to FIG. 7, in some examples, IMD 16 determines a time interval between at least one of an atrial sensing event or an atrial pacing event ($A_{s/p}$) of an atrial chamber of heart 12 and a ventricular sensing event ($V_s$) of a ventricular chamber of heart 12. For example, the time interval may be determined as follows:

$$T_{A-V} = T(V_s) - T(A_{s/p}) \quad \text{Equation (1)}$$

In Equation (1), $T_{A-V}$ is the time interval between at least one of an atrial sensing event or an atrial pacing event ($A_{s/p}$) of an atrial chamber of heart 12 and a ventricular sensing event ($V_s$) of a ventricular chamber of heart 12. In addition, in Equation (1), $T(V_s)$ is the time at which a ventricular sensing event is sensed, while $T(A_{s/p})$ is the time of an atrial sensing event or an atrial pacing event. IMD 16 may determine time interval $T_{A-V}$ while pacing therapy to heart 12, or a portion of heart 12 (e.g., left ventricle 32 and right ventricle 28), is suspended. In such an example, the time interval $T_{A-V}$ may be representative of a time between depolarization of an atrial chamber of heart 12 (i.e., intrinsic depolarization or depolarization due to a pacing pulse) and intrinsic depolarization of a ventricular chamber of heart 12 (i.e., without pacing the ventricular chamber).

In some examples, IMD 16 (or another device, such as programmer 24 or another computing device) determines the left-ventricular pacing interval and the right-ventricular pacing interval based on the time interval. For example, IMD 16 may determine a left-ventricular pacing interval that is based on the time interval, but less than the time interval. In accordance with this example, the left-ventricular pacing interval may be determined as follows:

$$A_{s/p} - LV_P = T_{A-V} - X \quad \text{Equation (2)}$$

In Equation (2), the variable "X" may be greater than zero but less than $T_{A-V}$. When bounded in this range, the left-ventricular pacing interval is a non-zero time interval that is less than the time interval $T_{A-V}$. As described in greater detail below, either IMD 16 or a clinician may select a value for "X." In some examples, a value for "X" may range between approximately 40 milliseconds and approximately 100 milliseconds, although other values are contemplated. In some example, "X" may be greater than or equal to the duration of a P-wave (e.g., sensed via electrodes within right atrium 26, or a far field sensing arrangement) that is determined while IMD 16 is not delivering pacing pulses to right atrium 26. In applications in which IMD 16 delivers a pacing pulse to left ventricle 32 based on a left-ventricular pacing interval determined in accordance with Equation (2), where "X" is greater than or equal to the duration of a P-wave that is determined while IMD 16 is not delivering pacing pulses to the atrial chambers of heart 12, IMD 16 may deliver a pacing pulse to left ventricle 32 before the ventricle is intrinsically depolarized via conduction from the AV node.

In some examples, IMD 16 (or another device, such as programmer 24 or another computing device) also determines a right-ventricular pacing interval based on the time interval $T_{A-V}$. For example, IMD 16 may determine a right-ventricular pacing interval that is based on the time interval, and is greater than the left-ventricular pacing interval, but less than the time interval $T_{A-V}$. In accordance with this example, the right-ventricular pacing interval may be determined as follows:

$$A_{s/p} - RV_P = T_{A-V} - Y \quad \text{Equation (3)}$$

In Equation (3), the variable "Y" may be greater than $A_{s/p}$-$LV_P$ but less than $T_{A-V}$. When bounded in this range, the right-ventricular pacing interval is a non-zero time interval that is less than the time interval $T_{A-V}$. As described in greater detail below, either IMD 16 or a clinician may select any suitable value for "Y." In general, the variable "Y" in Equation (3) is greater than the variable "X" in Equation (2). In some examples, a value for "Y" ranges between approximately "X"+10 milliseconds and approximately "X"+20 milliseconds, where "X" is determined in accordance with Equation (2). In some examples, a value for "Y" may range between approximately 50 milliseconds and approximately 110 milliseconds, although other values are contemplated.

In some examples, IMD 16 (or another device, such as programmer 24 or another computing device) automatically determines a value for "X" (Equation (2)) and/or a value for "Y" (Equation (3)) based on a monitored characteristic indicative of dyssynchrony between left ventricle 32 and right ventricle 28. For example, IMD 16 may deliver a pacing pulse to left ventricle 32 using an initial left-ventricular pacing interval and deliver a pacing pulse to right ventricle 28 using an initial right ventricular pacing interval. IMD 16 (or another device) may determine the initial left-ventricular pacing interval in accordance with Equation (2) above and the initial right-ventricular pacing interval in accordance with Equation (3) above using stored initial values for "X" and "Y." The stored initial value for "X" may be any suitable value greater than zero but less than $T_{A-V}$ such as, for example, an arbitrary value, a value found to be suitable in clinical experience, or the duration of a P-wave that is determined while IMD 16 is not delivering pacing pulses to the atrial chambers of heart 12. The stored initial value for "Y" may be any suitable value greater than "X" but less than $T_{A-V}$ such as, for example, an arbitrary value, a value found to be suitable in clinical experience, or the duration of a P-wave that is determined while IMD 16 is not delivering pacing pulses to the atrial chambers of heart 12. IMD 16 (or another device) may then monitor a characteristic indicative of dyssynchrony between left ventricle 32 and right ventricle 28 while IMD 16 delivers a pacing pulse to left ventricle 32 using the initial left-ventricular pacing interval and delivers a pacing pulse to right ventricle 28 using the initial right ventricular pacing interval.

In one example, IMD 16 (or another device) senses electrical signals attendant to the depolarization and repolarization of heart 12 (e.g., electrogram (EGM) signals or electrocardiogram (ECG) signals) while IMD 16 is delivering pacing pulses to left ventricle 32 and right ventricle 28 based on the initial left-ventricular pacing interval and the initial right-ventricular pacing interval, respectively. IMD 16 (or another device) then compares a morphological feature of the sensed signals to a stored baseline signal of heart 12 that is sensed while IMD 16 is not delivering pacing pulses to left ventricle 32 and right ventricle 28. For instance, IMD 16 (or another device) may compare the duration of a QRS-complex (e.g., of an EGM) of heart 12 that is sensed while IMD 16 delivers pacing pulses to left ventricle 32 and right ventricle 28 using the initial left-ventricular pacing interval and the initial right ventricular pacing interval, respectively, to the duration of a QRS-complex of heart 12 that sensed while IMD 16 is not delivering pacing pulses to left ventricle 32 and right ventricle 28. An increase in the duration of the QRS-complex while IMD 16 delivers pacing pulses to left ventricle 32 and right ventricle 28 as compared to when IMD 16 is not delivering pacing pulses to the ventricles may indicate that left ventricle 32 and right ventricle 28 are contracting out of phase due to the pacing pulses delivered by IMD 16.

In some examples, IMD 16 (or another device) adjusts the variables "X" and/or "Y" based on the sensed signals. For example, IMD 16 (or another device) may adjust "X" and/or "Y" (e.g., by sequentially incrementing or decrementing "X" and/or "Y" by a predetermined value, or by using any other technique) and may further determine an updated left-ventricular pacing interval and/or an updated right-ventricular pacing interval based on the adjusted "X" and/or "Y." IMD 16 may then deliver a left ventricular pacing pulse and a right ventricular pacing pulse based on the updated left-ventricular pacing interval and the updated right-ventricular, respectively. IMD 16 (or another device) may then compare the duration of a QRS-complex of heart 12 that is sensed while IMD 16 delivers the pacing pulses to, e.g., a value stored in memory or the duration of a QRS-complex of heart 12 that is sensed while IMD 16 is not delivering pacing pulses to left ventricle 32 and right ventricle 28. IMD 16 (or another device) can continue adjusting the variables "X" and/or "Y" until a suitable dyssynchrony is achieved which may be identified. In some examples, IMD 16 (or another device) selects a value for "X" and "Y" that, when used to deliver pacing therapy to heart 12, resulted in a QRS-complex that exhibited a duration above a threshold value or a QRS-complex duration that was the highest among all tested pacing intervals. In this manner, IMD 16 (or another device) can automatically determine a value for "X" and/or "Y."

In some examples, IMD 16 (or another device) monitors a different characteristic indicative of dyssynchrony between left ventricle 32 and right ventricle 28 in addition to or in lieu of monitoring an electrical signal attendant to the depolarization and repolarization of heart 12. For instance, in one example, therapy system 10 includes one or more sensors that are capable of monitoring a hemodynamic characteristic indicative of blood movement through patient 14. As briefly described above, some patients, such as patients with diastolic heart failure, may have ventricular dysfunction, whereby the ventricles cannot fully relax during diastole. Pacing therapy delivered by IMD 16 as described herein may help alleviate diastolic heart failure by pacing left ventricle 32 and right ventricle 28 so that the ventricles contract and relax out of phase (i.e., initiate the contraction and relaxation at different times). When left ventricle 32 and right ventricle 28 contract and relax out of phase (or at least partially out of phase) for such a patient, a volume of blood output by heart 12 may increase relative to when pacing therapy is not delivered. For this reason, it may be useful for if IMD 16 (or another device) determines "X" and/or "Y" based on a monitored hemodynamic characteristic.

In accordance with this example, therapy system 10 includes one or more sensors (not illustrated in FIG. 1) that are capable of monitoring a hemodynamic characteristic of patient 14. For example, therapy system 10 may include an optical perfusion sensor, an oxygen saturation sensor, an ultrasonic flow sensor, a pressure sensor, an ultrasonic probe, an accelerometer, a microphone, a hematocrit sensor or any other sensor adapted to sense one or more hemodynamic characteristics of patient 14. The sensor may be internal to patient 14 (e.g., integrated with IMD 16 or leads 18, 20, 22, or physically separate from IMD 16 or leads 18, 20, 22) or external to a patient 14. For example, therapy system 10 may include a pressure sensor carried by RV lead 18 that is configured to measure a pressure in right ventricle 28 and/or a pressure sensor carried by LV lead 20 that is configured to measure a pressure in left ventricle 32. In another example, therapy system 10 includes a sensor that is configured to measure a blood pressure (e.g., a mean arterial pressure) of patient 14.

In some examples, IMD 16 (or another device) monitors a hemodynamic characteristic of patient 14 that is sensed via a sensor of therapy system 10 while IMD 16 delivers pacing pulses to left ventricle 32 and right ventricle 28 based on initial left-ventricular pacing interval and an initial right-ventricular pacing interval, respectively, as described above. IMD 16 (or another device) then compares the monitored hemodynamic characteristic to a hemodynamic characteristic of patient 14 that is monitored while IMD 16 is not delivering pacing pulses to left ventricle 32 and right ventricle 28. For instance, in one example, IMD 16 (or another device) compares a pressure within left ventricle 32 during diastole (e.g., as determined by monitoring an ECG or EMG of heart 12) to a pressure within left ventricle 32 while IMD 16 is not delivering pacing pulses to left ventricle 32 and right ventricle 28. A decrease in pressure in left ventricle 32 while IMD 16 delivers pacing pulses to left ventricle 32 and right ventricle 28 as compared to when IMD 16 is not delivering pacing pulses to the ventricles may indicate that left ventricle 32 is relaxing more fully during diastole, which may indicate an improvement in the mechanical efficiency of heart 12.

In another example, IMD 16 or another device) compares a pressure within right ventricle 28 during diastole (e.g., as determined by monitoring an ECG or EMG of heart 12) to a pressure within right ventricle 28 while IMD 16 is not delivering pacing pulses to left ventricle 32 and right ventricle 28. Similar to when a pressure is monitored in left ventricle 32, a decrease in the pressure in right ventricle 28 while IMD 16 delivers pacing pulses to left ventricle 32 and right ventricle 28 as compared to when IMD 16 is not delivering pacing pulses to the ventricles may indicate that right ventricle 28 is relaxing more fully during diastole, which may indicate an improvement in the mechanical efficiency of heart 12.

In other examples, IMD 16 (or another device) compares a pressure within left ventricle 32 during diastole (e.g., as determined by monitoring an ECG or EMG of heart 12) to a pressure within right ventricle 28 during diastole, where the pressure within left ventricle 32 is detected at substantially the same time as the pressure within right ventricle 28. This may be referred to as an interventricular pressure difference or an RV-LV pressure difference. An increase in the pressure difference between the two ventricles while IMD 16 delivers pacing pulses to left ventricle 32 and right ventricle 28 as compared to when IMD 16 is not delivering pacing pulses to the ventricles may indicate an increase in dyssynchrony between left ventricle 32 and right ventricle 28. Thus, in some examples, IMD 16 modifies the "X" and/or "Y" values until a desired increase in pressure difference between ventricles 28, 32 is detected.

In yet another example, IMD 16 (or another device) compares a mean atrial pressure of patient 14 that is monitored while IMD 16 delivers pacing pulses to left ventricle 32 and right ventricle 28 to a mean atrial pressure of patient 14 that is monitored while IMD 16 is not delivering pacing pulses to left ventricle 32 and right ventricle 28. An increase in the mean atrial pressure of patient 14 while IMD 16 delivers pacing pulses to left ventricle 32 and right ventricle 28 as compared to when IMD 16 is not delivering pacing pulses to the ventricles may indicate an increase in the mechanical efficiency of heart 12 due to increased dyssynchrony between left ventricle 32 and right ventricle 28. Thus, in some examples, IMD 16 modifies the "X" and/or "Y" values until a desired increase in mean atrial pressure of patient 14 is detected.

In another example, IMD 16 (or another device) determines that the "X" and "Y" values are suitable based on a signal generated by a tissue perfusion sensor. When ventricular dyssynchrony is achieved, cardiac output of heart 12 may increase. Thus, tissue perfusion may increase. Thus, in some examples, IMD 16 modifies the "X" and/or "Y" values until a desired increase in tissue perfusion is detected.

Independent of the specific hemodynamic parameter sensed via a sensor in therapy system 10 and compared by IMD 16 (or another device), in some examples, IMD 16 (or another device) adjusts "X" and/or "Y" based on the sensed hemodynamic parameter. For example, IMD 16 (or another device) may adjust "X" and/or "Y" (e.g., by sequentially incrementing or decrementing "X" and/or "Y" by a predetermined value, or by using any other technique) and may further determine an updated left-ventricular pacing interval and/or an updated right-ventricular pacing interval based on the adjusted "X" and/or "Y." IMD 16 may then deliver a left ventricular pacing pulse and a right ventricular pacing pulse based on the updated left-ventricular pacing interval and the updated right-ventricular, respectively. IMD 16 (or another device) may then compare a hemodynamic parameter that is sensed while IMD 16 delivers the pacing pulses to, e.g., a value stored in memory or a hemodynamic parameter that sensed while IMD 16 is not delivering pacing pulses to left ventricle 32 and right ventricle 28. IMD 16 (or another device) can continue adjusting "X" and "Y" until a suitable dyssynchrony is achieved. In some examples, IMD 16 (or another device) selects a value for "X" and "Y" that, when used to deliver pacing therapy to heart 12, resulted in a hemodynamic parameter above a threshold value or a hemodynamic parameter that was the highest or lowest among all tested pacing intervals.

IMD 16 (or another device, such as programmer 24 or another computing device) may determine a left-ventricular pacing interval and a right-ventricular pacing interval, as described herein, using suitable techniques other than those described above. In another example, IMD 16 (or another device, such as programmer 24 or another computing device) determines right-ventricular pacing interval $A_{S/P}$-$RV_P$ based on a determined left-ventricular pacing interval $A_{S/P}$-$LV_P$ (e.g., which may be determined according to one or more the techniques outlined above). For example, IMD 16 may determine a right-ventricular pacing interval as follows:

$$A_{s/p}\text{-}RV_P = (A_{s/p}\text{-}LV_P) + Z \qquad \text{Equation (4)}$$

In Equation (4), the variable "Z" may be greater zero and may be selected so that the right-ventricular pacing interval $A_{s/p}$-$RV_P$ is less than the time interval $T_{A\text{-}V}$. When bounded in this range, the right-ventricular pacing interval is a non-zero time interval that is less than the time interval $T_{A\text{-}V}$. Either IMD 16 or a clinician may select any suitable value for "Z." In some examples, a value for may range "Z" between approximately 20 milliseconds and approximately 40 milliseconds, although other values are contemplated. For example, a suitable value for "Z" may vary based on the positioning of RV lead 18 within heart 12 as well as other factors.

In some examples, IMD 16 delivers pacing pulses to left ventricle 32 and right ventricle 28 based on the determined left-ventricular and right-ventricular pacing intervals. IMD 16 may detect of at least one of an atrial sensing event or an atrial pacing event ($A_{s/p}$) of an atrial chamber (e.g., right atrium 26 or left atrium 36) of heart 12. IMD 16 may then deliver a left-ventricular pacing pulse ($LV_P$) to left ventricle 32 upon expiration of the left-ventricular pacing interval, where the left-ventricular pacing interval begins at detection of at least one of the atrial sensing event or the atrial pacing event ($A_{s/p}$). IMD 16 may further deliver the right-ventricular pacing pulse ($RV_P$) to right ventricle 28 upon expiration of the right-ventricular pacing interval, where the right-ventricular pacing interval begins at detection of the same atrial sensing event or atrial pacing event ($A_{s/p}$). In this way, the pacing pulse delivered to left ventricle 32 ($LV_P$) is delivered before the pacing pulse delivered to right ventricle 28 ($RV_P$). Further, the pacing pulse to left ventricle 32 and the pacing pulse to right ventricle 28 are both delivered before either ventricle is intrinsically depolarized via conduction from the atrioventricular (AV) node and Purkinje system.

Such a pacing scheme may result in dyssynchronous activation and contraction of left ventricle 32 and right ventricle 28. The dyssynchronous activation and contraction of left ventricle 32 and right ventricle 28 may allow the two ventricles to expand within the pericardium of heart 12 at different times during diastole. For some patients, such as some patients suffering from diastolic heart failure, the pacing scheme may allow each ventricle to more fully relax and fill with blood, thereby improving the mechanical pumping efficiency of heart 12, compared to situations in which the pacing scheme was not applied to left ventricle 32 and right ventricle 28.

In some examples, IMD 16 delivers a single pacing pulse to left ventricle 32 and a single pacing pulse to right ventricle 28 per cardiac cycle, although any suitable number of pacing pulses may be delivered to each ventricular chamber per cardiac cycle. As previously indicated, IMD 16 may deliver a left ventricle pacing pulse and a right ventricle pacing pulse based on an atrial sensing event or atrial pacing event ($A_{s/p}$). Further, IMD 16 may determine a left-ventricular pacing interval and a right ventricular pacing interval for pacing left ventricle 32 and right ventricle 28, respectively, and each pacing interval may be based on a time interval between an atrial sensing event or an atrial pacing event ($A_{s/p}$) and a ventricular sensing event ($V_s$).

Depending on the configuration of IMD 16, the atrial sensing event or atrial pacing event ($A_{s/p}$) may be a sensing event (e.g., a P-wave sensed via electrodes within right atrium 26) or a pacing event of right atrium 26 (e.g., a pacing pulse delivered to right atrium 26 via electrodes of lead 22) or a sensing event (e.g., a P-wave sensed via electrodes within left atrium 36) or a pacing event of left atrium 36 (e.g., a pacing pulse delivered to left atrium 36 via electrodes of lead 20). A ventricular sensing event ($V_s$) may be a sensing event of left ventricle 32 (e.g., a R-wave sensed via electrodes within left ventricle 32 on LV lead 20) or a sensing event of right ventricle 28 (e.g., a R-wave sensed via electrodes within right ventricle 32 on RV lead 18).

In one example, IMD 16 determines a left-ventricular pacing interval and a right ventricular pacing interval based on a time interval between an atrial sensing event or an atrial pacing event of right atrium 26 and a ventricular sensing event of right ventricle 28. In another example, IMD 16 determines a left-ventricular pacing interval and a right ventricular pacing interval based on a time interval between an atrial sensing event or an atrial pacing event of right atrium 26 and a ventricular sensing event of a left ventricle 36.

In some examples, IMD 16 determines a left-ventricular pacing interval and a right ventricular pacing interval based on a plurality of different time intervals. For example, IMD 16 may determine a first time interval between an atrial sensing event or an atrial pacing ($A_{s/p}$) event of an atrial chamber of heart 12 and a ventricular sensing event of left ventricle 32 ($LV_s$). This first time interval may also be referred to as an $A_{s/p}$-$LV_s$ interval. IMD may further determine a second time interval between an atrial sensing event or an atrial pacing event ($A_{s/p}$) of an atrial chamber of heart 12 and a ventricular sensing event of right ventricle 28 ($RV_s$). This second time interval may also be referred to as an $A_{S/p}$-$RV_s$ interval. In accordance with this example, the atrial sensing event or atrial pacing event ($A_{s/p}$) for the first time interval and the second time interval may be the same atrial sensing event or atrial pacing event (e.g., detected during the same cardiac cycle) or different atrial sensing events or atrial pacing events (e.g., detected during different cardiac cycles). Further, the atrial sensing event or atrial pacing event ($A_{s/p}$) for the first time interval and second time interval may be for the same atrium (e.g., right atrium 26, or left atrium 36) of heart 12 or for different atria of heart 12.

In any event, the first time interval may be representative of the time between depolarization of an atrial chamber of heart 12 (i.e., intrinsic depolarization or depolarization due to a pacing pulse) and intrinsic depolarization of left ventricle 32 (i.e., without pacing the ventricular chamber), while the second time may be representative of the time between depolarization of an atrial chamber of heart 12 and intrinsic depolarization of right ventricle 28 (i.e., without pacing the ventricular chamber). IMD 16 may determine the left-ventricular pacing interval based on the first time interval, where the left-ventricular pacing interval is less than the first time interval. In addition, IMD 16 may determine the right-ventricular pacing interval based on the second time interval, where the right-ventricular pacing interval is greater than the left-ventricular pacing interval and less than the second time interval. In applications in which IMD 16 delivers pacing pulses to left ventricle 32 and right ventricle 28 based on the determined left-ventricular pacing interval and the determined right-ventricular pacing interval (e.g., based on an atrial sensing event or an atrial pacing ($A_{s/p}$) event during a different cardiac cycle than the cardiac cycle(s) during which the first time interval and second time interval were determined), IMD 16 may dyssynchronously activate left ventricle 32 and right ventricle 28, which may result in dyssynchronous contraction of the ventricles 32, 28.

In some examples, IMD 16 may determine a left-ventricular pacing interval ($A_{P/S}$-$LV_P$) and a right-ventricular pacing interval ($A_{P/S}$-$RV_P$) such that a time delay between a pacing pulse delivered to left ventricle 32 based on the left-ventricular pacing interval and a pacing pulse delivered to right ventricle 28 based on the right-ventricular pacing interval is maximized. That is, IMD 16 may maximize the duration between a right ventricular pacing event and a left ventricular pacing event within other pacing constraints. This may be referred to as a maximum $RV_p$-$LV_p$ delay.

In example of Equations (2) and (3) above, the left-ventricular pacing interval ($A_{P/S}$-$LV_P$) is determined by subtracting the variable "X" from the time interval $T_{A-V}$, where $T_{A-V}$>X>0. Further, the right-ventricular pacing interval ($A_{P/S}$-$RV_P$) is determined by subtracting the variable "Y" from the $T_{A-V}$, where $T_{A-V}$>Y>$A_{s/p}$-$LV_p$. Consequently, in this example, the $RV_p$-$LV_p$ delay may be maximized as "X" approaches zero and "Y" approaches $T_{A-V}$. For instance, when IMD 16 delivers a left-ventricle pacing pulse ($LV_P$) substantially immediately after an atrial sensing event or atrial pacing event ($A_{s/p}$), and IMD 16 delivers a right-ventricle pacing pulse ($RV_p$) substantially immediately before $T_{A-V}$ (i.e., a time immediately before the ventricles of heart 12 are intrinsically depolarized via conduction from the atrioventricular (AV) node), IMD 16 may maximize the $RV_p$-$LV_p$ within the pacing constraints of Equations (2) and (3). Such a pacing scheme may maximize a phase shift between the activation and contraction of left ventricle 32 and right ventricle 28. That is, the pacing scheme may maximize the dyssynchrony of left ventricle 32 and right ventricle 28.

The dyssynchronous pacing therapy provided by IMD 16 may be useful for patients with heart failure. In a normal electrical activation sequence, left ventricle 32 contacts and relaxes in synchrony with right ventricle 28. During the contraction phase, which is referred to as systole, pressure rises in left ventricle 32 and right ventricle 28 as each ventricle isovolumetrically contracts. Pressure continues rising in left ventricle 32 and right ventricle 28 until the pulmonary and aortic valves of heart 12 open. At this point, pressurized blood ejects from left ventricle 32 and right ventricle 28. Pressurized blood continues ejecting until the end of contraction. The amount of blood remaining in left ventricle 32 and right ventricle 28 at the end of contraction is referred to as the left and right end-systolic volume, respectively.

Following contraction, left ventricle 32 and right ventricle 28 relax and refill with blood, which is referred to as diastole. The ventricles continue refilling with blood until another contraction, repeating the cycle outlined above. The volume of blood in left ventricle 32 and right ventricle 28 immediately before another contraction is referred to as the left and right end-diastolic volume, respectively.

Some patients, such as patients with diastolic heart failure, may have ventricular dysfunction, whereby the ventricles become stiff and cannot fully relax during diastole. As a result of this dysfunction, the ventricles may not fully fill or may abnormally fill during diastole. For example, a patient with diastolic heart failure may have at least one ventricle that exhibits an ejection fraction less than approximately 35 percent, where the ejection fraction is calculated by dividing the end-systolic volume of the ventricle by the end-diastolic volume of the ventricle. By contrast, a healthy individual may have ventricles that each exhibit an ejection fraction greater than approximately 50 percent.

Pacing therapy delivered by IMD 16 may help alleviate diastolic heart failure by pacing left ventricle 32 and right ventricle 28 so that the ventricles contract and relax out of phase (i.e., initiate the contraction and relaxation at different times). Left ventricle 32 and right ventricle 28 are enclosed within the pericardium, which is a sac that surrounds heart 12. During simultaneous relaxation of left ventricle 32 and right ventricle 28, the two ventricles may compete for space within the pericardium. For example, for some patients with diastolic heart failure, one ventricle may only increase in size by reducing the space occupied by to the other ventricle. This space competition may contribute to the impaired filling of left ventricle 32 and right ventricle 28 during diastole. However, when IMD 16 paces left ventricle 32 and right ventricle 28 so that the ventricles contract and relax out of phase, left ventricle 32 and right ventricle 28 may separately relax within the pericardium without consuming at least some of or all of the space otherwise devoted to the other ventricle.

IMD 16 may indefinitely deliver pacing therapy to heart 12 according to a predetermined left-ventricular pacing interval and a determined right-ventricular pacing interval, as described herein. In some situations, such as when the heart rate of patient 14 changes, the time interval $T_{A\text{-}V}$ may change from an initially determined value. Accordingly, it may be useful for IMD 16 to periodically evaluate the time interval $T_{A\text{-}V}$, the left-ventricular pacing interval, and the right ventricular-pacing interval in order to maintain delivery of the left-ventricular pacing pulse ($LV_P$) and the right-ventricular pacing pulse ($RV_P$) at times that result in suitable dyssynchrony between left ventricle 32 and right ventricle 28.

In some examples, IMD 16 delivers pacing pulses to left ventricle 32 based on a particular left-ventricular pacing interval and right ventricle 28 based on a particular right-ventricular pacing interval for a predetermined number of cardiac cycles or for a predetermined period of time. For example, after IMD 16 delivers pacing pulses to left ventricle 32 and right ventricle 28 for a predetermined number of cardiac cycles or for a predetermined period of time, IMD 16 may reevaluate the time interval $T_{A\text{-}V}$, the left-ventricular pacing interval, and the right-ventricular pacing interval, as necessary. The number of cardiac cycles or predetermined period of time may be selected to be any clinically appropriate value and may be specific to patient 14 or general to more than one patient. In some examples, IMD 16 may reevaluate the time interval $T_{A\text{-}V}$, the left-ventricular pacing interval, and the right-ventricular pacing interval after a set number of minutes such as, e.g., 1 minute, 2 minutes, 5, minutes, or the like, although other times are contemplated.

As described above, in some situations, the time interval $T_{A\text{-}V}$ may change from an initially determined value when the heart rate of patient 14 changes, e.g., due to a change in the activity level of patient 14. Accordingly, in some examples, IMD 16 delivers pacing pulses to left ventricle 32 based on a particular left-ventricular pacing interval and right ventricle 28 based on a particular right-ventricular pacing interval until an activity level of patient 14 changes. For example, IMD 16 may monitor a signal from an accelerometer (or any other sensor that generates a signal that varies based on the activity level of patient 14) and compare a sample of the signal to one or more amplitude thresholds. IMD 16 may identify each threshold crossing as an activity count and may identify crossing of higher amplitudes as multiple activity counts. Upon detecting a predetermined number of activity counts, IMD 16 may reevaluate the time interval $T_{A\text{-}V}$, the left-ventricular pacing interval, and the right-ventricular pacing interval, as necessary.

Depending on the technique used to deliver pacing therapy and the configuration of IMD 16, IMD 16 may reevaluate the time interval $T_{A\text{-}V}$, the left-ventricular pacing interval, and the right-ventricular pacing interval in a variety of different ways. In one example, IMD 16 suspends pacing therapy to left ventricle 32 and right ventricle 28 for a cardiac cycle. IMD 16 then detects an atrial sensing event or atrial pacing event ($A_{S/P}$) in an atrium of heart 12 while the pacing therapy is suspended. For example, IMD 16 may sense a P-wave via electrodes positioned within right atrium 26 and/or left atrium 36, or IMD 16 may detect delivery of a pacing pulse to right atrium 26 and/or left atrium 36. IMD 16 may additionally detect a ventricular sensing event ($V_s$) in a ventricle of heart 12. For example, IMD 16 may sense an R-wave via electrodes positioned within left ventricle 32 (e.g., on LV lead 20) and/or right ventricle 28 (e.g., on RV lead 18). IMD 16 may determine an updated time interval $T_{A\text{-}v}$ using Equation (1) above, based on the detected atrial sensing event or atrial pacing event ($A_{s/p}$) and the detected ventricular sensing event ($V_s$). If the updated time interval $T_{A\text{-}V}$ is different than the initially determined time interval $T_{A\text{-}V}$, IMD 16 may reevaluate the left-ventricular pacing interval ($A_{S/P}$-$LV_P$) and the right-ventricular pacing interval ($A_{P/S}$-$RV_P$) using Equations (2) and (3) above. IMD 16 may resume delivery of the left-ventricle pacing pulse and the right-ventricle pacing pulse based on the reevaluated left-ventricular pacing interval and the right-ventricular pacing interval, respectively, on the next cardiac cycle.

In some additional examples, IMD 16 may suspend pacing therapy to left ventricle 32 and right ventricle 28 for a plurality of cardiac cycles. IMD 16 may then detect a plurality of an atrial sensing events or atrial pacing events ($A_{S/P}$) and a plurality of ventricular sensing events ($V_s$) while the pacing therapy is suspended. For example, IMD 16 may detect one atrial sensing event or one atrial pacing event and one ventricular sensing event per cardiac cycle for a plurality of cardiac cycles. IMD 16 may determine an updated time interval $T_{A\text{-}V}$, left-ventricular pacing interval, and right-ventricular pacing interval based on the plurality of atrial sensing events or atrial pacing events ($A_{S/P}$) and the plurality of ventricular sensing events ($V_s$). For example, IMD 16 may determine a time interval $T_{A\text{-}V}$ for each of the plurality of cardiac cycles based on an atrial sensing event or atrial pacing event ($A_{S/P}$) and a ventricular sensing event ($V_s$) from each cardiac cycle. From the plurality of determined time intervals $T_{A\text{-}V}$, IMD 16 may determine, for example, a mean, median, smallest, and/or largest time interval $T_{A\text{-}V}$. IMD 16 may select one of these determined time intervals $T_{A\text{-}V}$ for comparison with the initially determined time interval $T_{A\text{-}V}$ (i.e., before the suspension of pacing therapy). IMD 16 may determine if time interval $T_{A\text{-}V}$ has changed, and, if so, modify the left-ventricular pacing interval ($A_{P/S}$-$LV_P$) and the right-ventricular pacing interval ($A_{P/S}$-$RV_P$) as described above. In addition, IMD 16 may resume pacing therapy by delivering a left-ventricle pacing pulse ($LV_P$) and right-ventricle pacing pulse ($RV_P$) based on the modified left-ventricular pacing interval and modified right-ventricular pacing interval, respectively.

In some examples, IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 is programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that presents information to and receives input from a user. In some examples, a user may interact with programmer 24 remotely via a networked computing device.

A user, such as a physician, technician, surgeon, electrophysiologist, other clinician, or patient, may interact with programmer 24 to communicate with IMD 16. For example, the user may interact with programmer 24 to retrieve physiological or diagnostic information from IMD 16. A user may also interact with programmer 24 to program IMD 16 by, e.g., selecting values for operational parameters of the IMD.

For example, the user may use programmer 24 to retrieve information from IMD 16 regarding the rhythm of heart 12, trends thereof over time, intrinsic conduction times of heart 12, or tachyarrhythmia episodes. As another example, the user may use programmer 24 to retrieve information from IMD 16 regarding other sensed physiological parameters of patient 14, such as sensed electrical activity, sensed hemodynamic conditions, intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
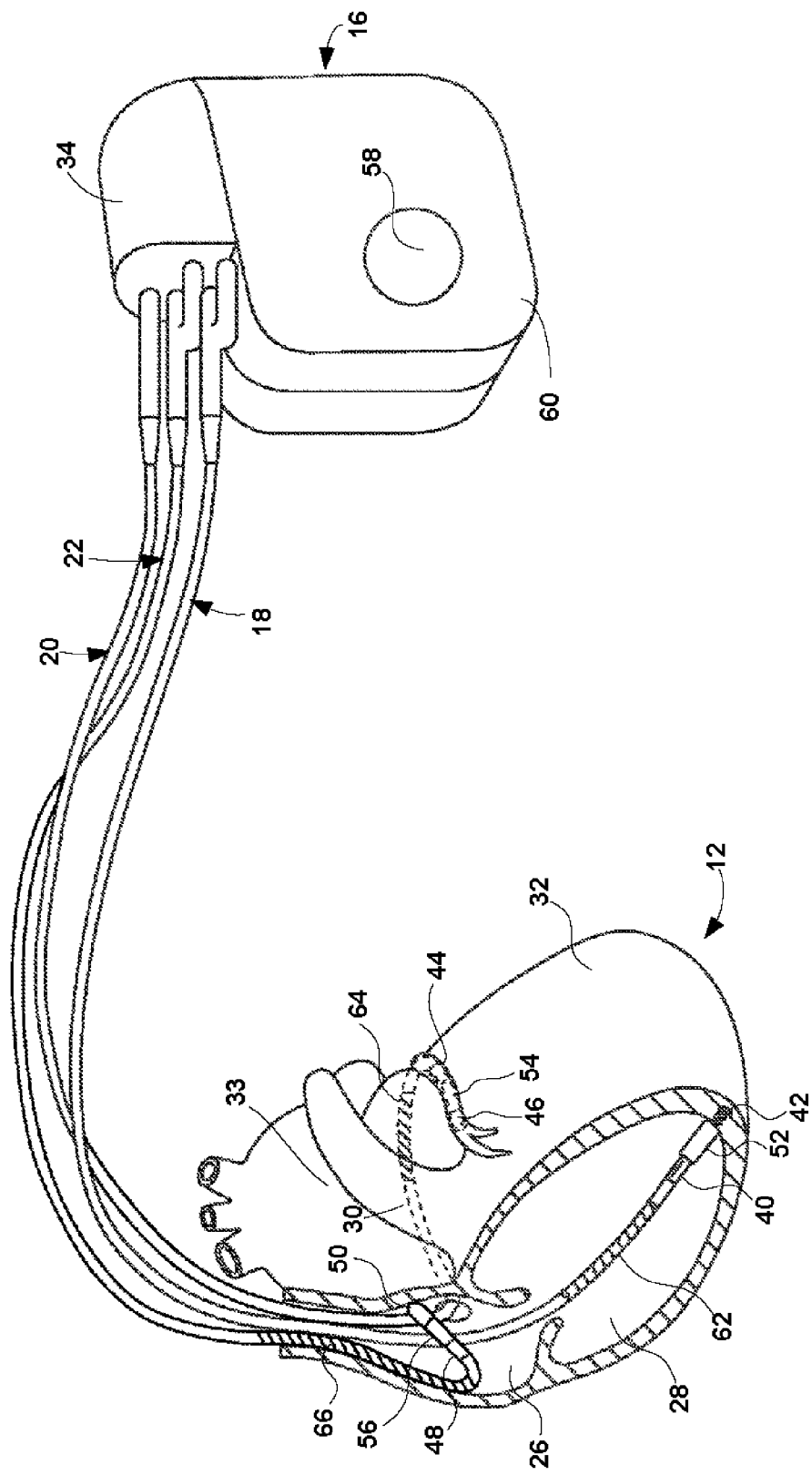
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a stimulation generator and a sensing module of IMD 16 via connector block 34. In some examples, proximal ends of leads 18, 20, 22 may include electrical contacts that electrically couple to respective electrical contacts within connector block 34 of IMD 16. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths, although leads 18, 20, 22 may have other configurations (e.g., may not include coiled conductors) in other examples. In the illustrated example, bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

Helix tip electrode 50, which may be extendable or preexposed, of RA lead 22 may be inserted into the tissue of right atrium 26 to substantially fix RA lead 22 within right atrium 26. For example, helix tip electrode 50 may be inserted into or proximate to the endocardium of the septum that separates right atrium 26 and left atrium 36 at a posterior portion of right atrium 26. As described previously, RA lead 22 may be positioned such that RA lead 22 may sense electrical activity within right atrium 26, and, in some examples, pace right atrium 26, and also deliver a stimulation signal to (or proximate to) the AV node, e.g., to (or proximate to) the AV nodal vagal fat pad. Helix tip electrode 50 may aid in maintaining RA lead 50 in the appropriate position to provide such functionality.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a stimulation generator that generates therapeutic stimulation, such as cardiac pacing pulses, defibrillation shocks, and/or cardioversion shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials usable in implantable defibrillation electrodes.

The configuration of system 10 illustrated in FIGS. 1 and 2 is merely one example. In other examples, a therapy system may include extravascular electrodes, such as subcutaneous electrodes, epicardial electrodes, and/or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may deliver defibrillation pulses, pacing pulses, and other therapies to heart 12 via percutaneous leads that extend through the skin of patient 14 to a variety of positions within or outside of heart 12.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. Other examples of systems may include a two-lead system with one lead extending from IMD 16 into left ventricle 32 another lead extending from IMD 16 to right ventricle 28. The lead extending from IMD 16 to right ventricle 28 in such a two-lead system may or may not include sensing and/or stimulation electrodes within right atrium 26. The lead extending from IMD 16 to left ventricle 32 in such a two-lead system may or may not include sensing and/or stimulation electrodes within right atrium 26 and/or left atrium 36. Other lead configurations are contemplated.

As previously indicated, a system may include leads that extend to any location within or proximate to heart 12. In some examples, a system may include at least one lead extending from IMD 16 to right ventricle 28, where at least one electrode on the lead is positioned adjacent the right lateral basal wall of heart 12. In some examples, when IMD 16 delivers a pacing pulse to right ventricle 28 with at least one electrode of RV lead 18 positioned adjacent the right lateral basal wall of heart 12 (in addition to delivering a pacing pulse to left ventricle 32), the pacing therapy provided by IMD 16 may cause greater dyssynchrony between left ventricle 32 and right ventricle 28 than when IMD 16 delivers a pacing pulse to other locations right ventricle 28.

Figure 3:
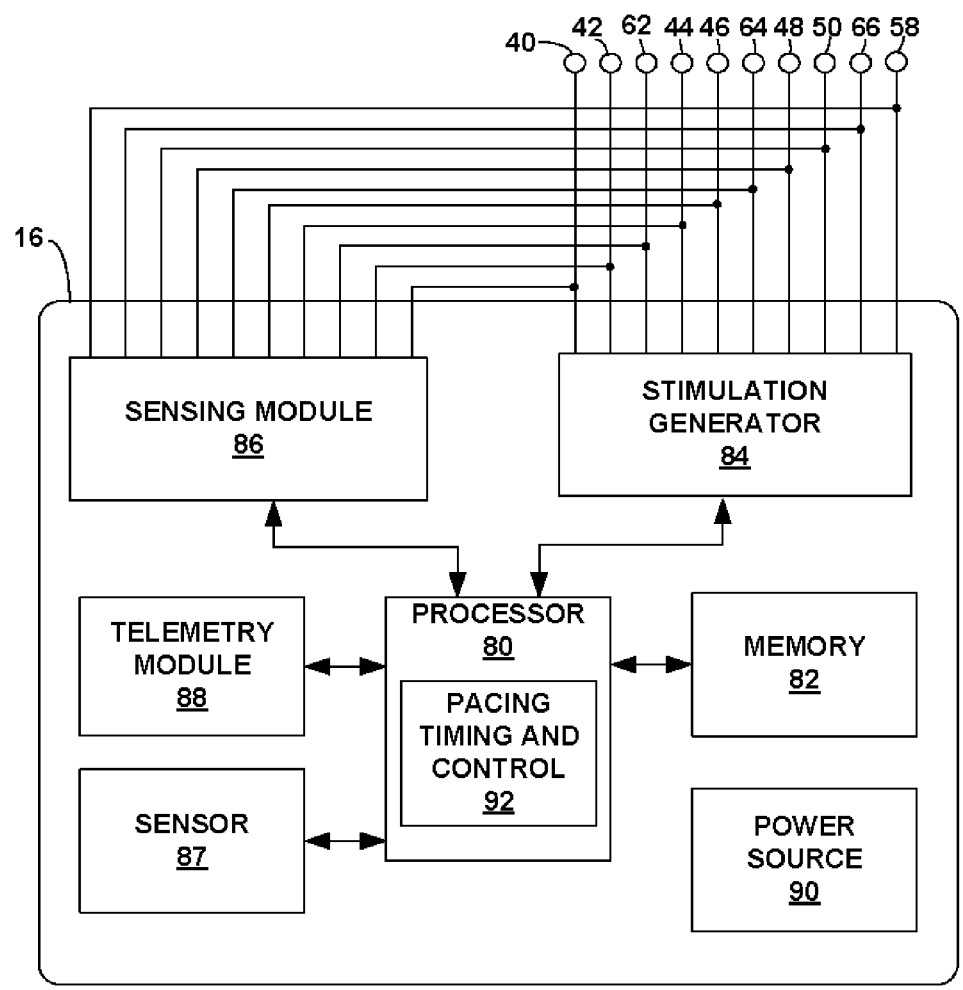
FIG. 3 is a functional block diagram illustrating an example configuration of the IMD of FIG. 1.

FIG. 3 is a functional block diagram of one example configuration of IMD 16, which includes processor 80, memory 82, stimulation generator 84, sensing module 86, sensor 87, telemetry module 88, and power source 90. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. In addition to sensed physiological parameters of patient 14 (e.g., electrogram (EGM) or electrocardiogram (ECG) signals), one or more timing intervals, left-ventricle pacing intervals, and/or right-ventricle pacing intervals may be stored by memory 82 for selection by processor 80. Further, as discussed above, one or more parameters (e.g., time intervals) for determining a left-ventricle pacing interval and a right-ventricle pacing interval may be stored in memory 82.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein, as well as other processors referred to herein, may be embodied as software, firmware, hardware or any combination thereof.

Processor 80 controls stimulation generator 84 to deliver stimulation therapy to heart 12 according to operational parameters or programs, which may be stored in memory 82. For example, processor 80 may control stimulation generator 84 to deliver electrical pulses with the amplitudes, pulse widths, frequency, or electrode polarities specified by one or more selected therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, stimulation generator 84 is configured to generate and deliver electrical stimulation therapy to heart 12. For example, under the control of processor 80, stimulation generator 84 may deliver pacing pulses to left ventricle 32 and right ventricle 28 of heart 12 (FIG. 2) in accordance with a left-ventricular pacing interval and a right-ventricular pacing interval determined in accordance with the techniques described herein. In some examples, stimulation generator 84 may also be configured to deliver cardioversion or defibrillation shocks to heart 12, which can also be done under the control of processor 80. In some examples, stimulation generator 84 delivers one or more of these types of stimulation in the form of electrical pulses. In other examples, stimulation generator 84 may deliver one or more of these types of stimulation in the form of other signals, such as sine waves, square waves, or other substantially continuous time signals.

In some examples, stimulation generator 84 includes a switch module and processor 80 uses the switch module to select, e.g., via a data/address bus, which of the available electrodes are used to deliver stimulation, e.g., defibrillation pulses or pacing pulses. The switch module may include a switch array, switch matrix, multiplexer, or any other type of switching device suitable to selectively couple a signal to selected electrodes. However, stimulation generator 84 may not include a switch module in other examples.

Sensing module 86 may monitor electrical signals from at least one of electrodes 40, 42, 44, 46, 48, 50, 58, 62, 64 or 66 in order to monitor electrical activity of heart 12. For example, sensing module 86 may sense atrial events (e.g., a P-wave) with electrodes 48, 50, 66 within right atrium 26, a left ventricle event (e.g., an R-wave) with electrodes 44, 46, 64 within left ventricle 32, and/or a right ventricle event (e.g., an R-wave) with electrodes 40, 42, 62 within right ventricle 28. In some examples, sensing module 86 includes a switch module to select which of the available electrodes are used to sense the heart activity. In these examples, processor 80 can select the electrodes that function as sense electrodes, i.e., selects the sensing configuration, via the switch module within sensing module 86, e.g., by providing signals via a data/address bus. In other examples, however, sensing module 86 does not include a switch module.

In some examples, sensing module 86 includes multiple detection channels, each of which may comprise an amplifier. Each sensing channel may detect electrical activity in respective chamber of heart 12, and may be configured to detect either R-waves or P-waves. In some examples, sensing module 86 or processor 80 may include an analog-to-digital converter for digitizing the signal received from a sensing channel for EGM signal processing by processor 80. In response to the signals from processor 80, the switch module within sensing module 86 (if present) may couple the outputs from the selected electrodes to one of the detection channels or the analog-to-digital converter.

Processor 80 may define variable intervals for timing the delivery of right ventricle pacing pulses ($RV_P$) and left ventricle pacing pulses ($LV_P$) based on signals from sensing module 86. These intervals may include, for example, intervals used to determine the left-ventricular pacing interval and the right-ventricular pacing interval (e.g., $A_{P/S}$-$V_S$). Signals generated by sensing module 86 may include, for example: an right atrium-event signal, which indicates a detection of a P-wave via sensing module 86; a left atrium-event signal, which indicates a detection of a P-wave via sensing module 86; a right ventricle-event signal, which indicates a detection of an R-wave via sensing module 86; or a left ventricle-event signal, which indicates a detection of an R-wave via sensing module 86.

In some examples, processor 80 detects a right atrium-event signal based on an electrical cardiac signal sensed by electrodes implanted within right atrium 26. However, in other examples, processor 80 may detect the right atrium-event signal based on an electrical cardiac signal sensed by electrodes outside of right atrium 26 (e.g., within right atrium 26, right ventricle 28 or left atrium 36). In addition, in some examples, processor 80 detects the left atrium-event signal based on an electrical cardiac signal sensed by electrodes implanted within left atrium 36 (FIG. 1), while in other examples processor 80 detects the left atrium-event signal based on an electrical cardiac signal sensed by electrodes outside of left atrium 36 (e.g., within right atrium 26, right ventricle 28 or left ventricle 32). In some examples, processor 80 detects a right ventricle-event signal based on an electrical cardiac signal sensed by electrodes implanted within right ventricle 28. However, in other examples, processor 80 may detect the right ventricle-event signal based on an electrical cardiac signal sensed by electrodes outside of right ventricle 28 (e.g., within right atrium 26, left ventricle 32 or left atrium 36). Similarly, in some examples, processor 80 can detect a left ventricle-event signal based on an electrical cardiac signal sensed by electrodes implanted within left ventricle 32 or based on an electrical cardiac signal sensed by electrodes implanted outside of left ventricle 32 (e.g., within right atrium 26, right ventricle 28, or left atrium 36).

In the example of therapy system 10 shown in FIGS. 1 and 2, IMD 16 is not connected to electrodes that are implanted within left atrium 36. However, in other example therapy systems, IMD 16 may be connected to electrodes that are implanted within left atrium 36 in order to sense electrical activity of left atrium 36.

An example of a pacing interval processor 80 may define based on these different types of signals generated by sensing module 86 is the interval of time following an atrial sense or pacing event ($A_{S/P}$) at which a pacing pulse is delivered to left ventricle 32 and a pacing pulse is delivered to right ventricle 28. As described above, these intervals may be referred to as the left-ventricular pacing interval ($A_{S/P}$-$LV_P$) and the right-ventricular pacing interval ($A_{S/P}$-$RV_P$), respectively. An example technique for determining the left-ventricular pacing interval and the right-ventricular pacing interval is described with reference to FIG. 6. As another example, processor 80 may define the time interval $T_{A-V}$, which is the time period between an atrial sense or pace event ($A_{S/P}$) and ventricular sensing event ($V_s$). Processor 80 may, for example, determine the time interval $T_{A-V}$ to be the time interval between a sensed P-wave sensed via electrodes (e.g., within right atrium 26) and an R-wave sensed via electrodes (e.g., within left ventricle 32). In another example, processor 80 may determine the time interval $T_{A-V}$ to be the time interval between a sensed P-wave sensed via electrodes (e.g., within right atrium 26) and an R-wave sensed via electrodes (e.g., within right ventricle 28). Other time intervals and sensing locations are contemplated are contemplated.

In some examples, processor 80 determines a plurality of time intervals $T_{A-V}$. In one example, processor 80 determines a first time interval $T_{A-LV}$ be the time interval between a P-wave sensed via electrodes within either right atrium 26 or left atrium 36 (FIG. 2) and an R-wave sensed via electrodes of lead 20 (FIG. 2) within left ventricle 32. Processor may determine a second time interval $T_{A-RV}$ be the time interval between a P-wave sensed via electrodes within either right atrium 26 or left atrium 36 (FIG. 2) and an R-wave sensed via electrodes of lead 18 (FIG. 2) within right ventricle 28. However the atrial sense event can be sensed with electrodes outside of the atrium 26 or 36, e.g., external electrodes or electrodes within one or both ventricles 28, 32. Similarly, the ventricular sense events discussed herein are primarily described as being sensed by electrodes within the ventricle, but can be sensed with electrodes outside the ventricle, such as one or more electrodes in another ventricle, in an atrium 26, 36, or outside heart 12 and/or event outside vasculature of patient 14.

In some examples, processor 80 defines a left-ventricular pacing interval ($A_{P/S}$-$LV_P$) and a right-ventricular pacing interval ($A_{P/S}$-$RV_P$) based on one or more time intervals $T_{A-V}$. For example, as described above with reference to Equations (2) and (3), processor 80 of IMD 16 may define a left-ventricular pacing interval ($A_{P/S}$-$LV_P$) and a right-ventricular pacing interval ($A_{P/S}$-$RV_P$) based on one or more time intervals $T_{A-V}$ and one or more variables stored in memory 82. In another example, processor 80 may define a left-ventricular pacing interval ($A_{P/S}$-$LV_P$) and a right-ventricular pacing interval ($A_{P/S}$-$RV_P$) to maximize an $RV_p$-$LV_p$ delay.

In other examples, processor 80 defines a left-ventricular pacing interval ($A_{P/S}$-$LV_P$) based on one or more time intervals $T_{A-V}$, and a right-ventricular pacing interval ($A_{P/S}$-$RV_P$) based on the determined left-ventricular pacing interval ($A_{P/S}$-$LV_P$). For example, as described above with reference to Equation (4), IMD 16 may define a right-ventricular pacing interval ($A_{P/S}$-$RV_P$) based on a left-ventricular pacing interval ($A_{P/S}$-$LV_P$) and one or more variables stored in memory 82.

Processor 80 may include pacing timing and control module 92, which may be embodied as hardware, firmware, software, or any combination thereof. Pacing timing and control module 92 may comprise a dedicated hardware circuit, such as an ASIC, separate from other processor 80 components, such as a microprocessor, or a software module executed by a component of processor 80 (e.g., a microprocessor or ASIC). Pacing timing and control module 92 may help define left-ventricular pacing interval ($A_{P/S}$-$LV_P$) and a right-ventricular pacing interval ($A_{P/S}$-$RV_P$) for controlling the delivery of a left ventricle pacing pulse ($LV_p$) and a right ventricle pacing pulse ($RV_p$), respectively. For example, pacing timing and control module 92 may include programmable counters or timers for determining one or more time intervals $T_{A-V}$, and/or any other relevant time intervals. In addition, pacing timing and control module 92 may include timers for timing the delivery of pacing pulses and other functions that are based on a pacing interval.

In examples in which IMD 16 delivers a left ventricle pacing pulse ($LV_p$) and a right ventricle pacing pulse ($RV_p$) a predetermined period of time following an atrial sense or pace event ($A_{P/S}$), pacing timing and control module 92 may include a timer that is loaded with the appropriate $A_{P/S}$-$LV_P$ and $A_{P/S}$-$RV_P$ intervals. The timer of pacing timing and control module 92 may be configured to begin upon the detection of a preceding atrial pace or sensing event ($A_{P/S}$). For example, upon expiration of one timer, processor 80 may control stimulation generator 84 to deliver a pacing pulse $LV_P$ to left ventricle 32 (FIG. 1), and upon expiration of another timer, processor 80 may control stimulation generator 84 to deliver a pacing pulse $RV_P$ to right ventricle 28 (FIG. 1). In some examples, pacing timing and control module 92 may generate a trigger signal that triggers the output of a pacing pulse by stimulation generator 84.

In examples in which IMD 16 is configured to deliver other types of cardiac rhythm therapy in addition to a left ventricle pacing pulse and a right ventricle pacing pulse, as described herein, pacing timing and control module 92 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In examples in which IMD 16 is configured to deliver other types of cardiac rhythm therapy in addition to a left ventricle pacing pulse and a right ventricle pacing pulse, as described herein, intervals defined by pacing timing and control module 92 within processor 80 may include atrial and ventricular pacing escape intervals, refractory periods during which sensed P-waves and R-waves are ineffective to restart timing of the escape intervals, and the pulse widths of the pacing pulses. As another example, pacing timing and control module 92 may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacing timing and control module of processor 80 may also determine the amplitude of the cardiac pacing pulses.

During pacing modes other than the left ventricle pacing and the right ventricle pacing described herein, escape interval counters within pacing timing and control module 92 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one or more of the chambers of heart 12. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals.

Processor 80 may also derive other physiological parameters from signals sensed via electrical sensing module 86. For example, processor 80 may establish one or more indicators of ejection fraction and/or heart failure status from electrical signals sensed via electrical sensing module 86. For example, impedance signals sensed via electrical sensing module 86 may be used to determine flow or pressure, which may indicate heart failure status with a preserved ejection fraction of heart 12. In some examples, IMD 16 may adjust a left-ventricular pacing interval ($A_{P/S}$-$LV_P$) and a right-ventricular pacing interval ($A_{P/S}$-$RV_P$) based on the indication of the preserved ejection fraction so as to minimize the preserved ejection fraction of heart 12. For example, as generally described above with respect to FIG. 1, IMD 16 (or another device, such as programmer 24 or another computing device) may monitor the preserved ejection fraction of heart 12 and determine a value for "X" in Equation (2) and a value for "Y" in Equation (3) that results in a suitable preserved ejection fraction. In some examples, IMD 16 (or another device) selects a value for "X" and "Y" that, when used to deliver pacing therapy to heart 12, resulted in an ejection fraction above a threshold value or an ejection fraction that was the highest among all tested pacing intervals.

In some examples, IMD 16 include one or more sensors 87 separate from electrodes 40, 42, 48, 50, 58, 62, and 66. Via a signal generated by sensor 87, processor 80 may monitor one or more parameters of patient 14 including, e.g., a hemodynamic parameter, an activity level, heart failure, ejection fraction, and/or other conditions. Examples of sensors 87 that may generate a signal indicative of an activity level of patient 14 include an accelerometer, a bonded piezoelectric crystal, a mercury switch, or a gyro. Processor 80 may also detect one or more hemodynamic parameters via one or more sensors 87. For example, sensors 87 may monitor blood pressure in one or more of right ventricle 28, left ventricle 32, another chamber of heart 12, and/or an artery of patient 14. As one example, one or more of sensors 87 may monitor blood pressure within a pulmonary artery of patient 14. Example sensors that may generate a signal indicative of a hemodynamic parameter include a sensor capable of detecting heart or blood sounds, an optical or ultrasonic sensor capable of detecting changes in flow associated with blood motion, or an optical sensor capable of detecting oxygen saturation or tissue perfusion changes associated with blood motion.

Processor 80 may automatically determine a value for "X" (Equation (2)) and/or a value for "Y" (Equation (3)) based on a signal generated by sensor 87. For example, as described above with reference to Equations (2) and (3), processor 80 of IMD 16 may define an initial left-ventricular pacing interval ($A_{P/S}$-$LV_P$) and an initial right-ventricular pacing interval ($A_{P/S}$-$RV_P$) based on initial "X" value and an initial "Y" value stored in memory 82. Processor 80 may then control stimulation generator 84 to deliver a left ventricle pacing pulse ($LV_P$) and a right ventricle pacing pulse ($RV_P$) a predetermined period of time following an atrial sense or pace event ($A_{P/S}$) based on the initial left-ventricular pacing interval ($A_{P/S}$-$LV_P$) and the initial right-ventricular pacing interval ($A_{P/S}$-$RV_P$). Processor 80 may receive and analyze signals generated by sensor 87. Processor 80 may further compare the signals, e.g., to a threshold value or to one or more baseline values sensed while IMD 16 was not delivering pacing therapy to heart 12, which can indicate whether the pacing delivered according to the current "X" and "Y" values results in suitable ventricular dyssynchrony, e.g., which improves cardiac output of heart 12 in a physiologically significant manner. In some examples, processor 80 adjusts the value for "X" and/or "Y" based on the signals generated by sensor 87, as described above with respect to FIG. 1.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 may transmit atrial and ventricular heart signals (e.g., EGM signals) produced by atrial and ventricular sensing amplification circuits within sensing module 86 to programmer 24. Other types of information may also be transmitted to programmer 24, such as the various intervals used to determine and/or deliver a pacing pulse to the left ventricle 32 and the right ventricle 28. Programmer 24 may interrogate IMD 16 to receive the heart signals. Processor 80 may store the heart signals within memory 82, and retrieve stored heart signals from memory 82. Processor 80 may also generate and store marker codes indicative of different cardiac episodes that sensing module 86 detects, and transmit the marker codes to programmer 24.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

Figure 4:
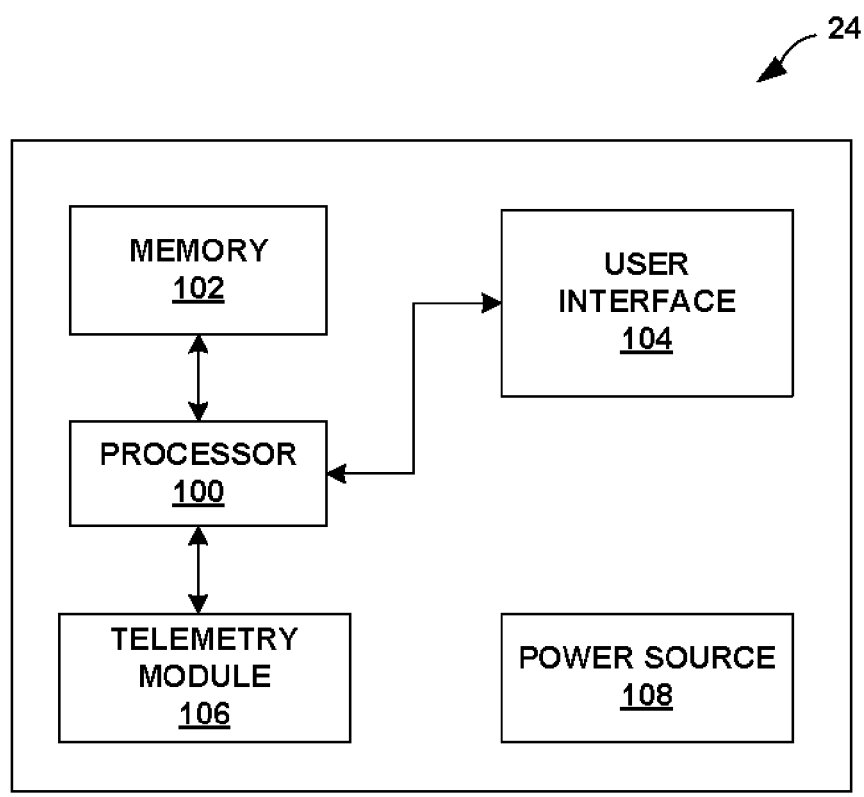
FIG. 4 is block diagram of an example external programmer that facilitates user communication with the IMD.

FIG. 4 is a functional block diagram of an example configuration of programmer 24. As shown in FIG. 4, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, or modify therapy programs for IMD 16. The clinician may interact with programmer 24 via user interface 104, which may include a display to present a graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Although techniques for determining a left-ventricular pacing interval ($A_{S/P}$-$LV_P$) and a right-ventricular pacing interval ($A_{S/P}$-$RV_P$) in order to achieve dyssynchronous activation and contraction of left ventricle 32 and right ventricle 28 (FIG. 1) are primarily described with respect to processor 80 (FIG. 3) of IMD 16, in other examples, processor 100 of programmer 24 can perform any part of the techniques described herein for determining a left-ventricular pacing interval ($A_{S/P}$-$LV_P$) and a right-ventricular pacing interval ($A_{S/P}$-$RV_P$), as well as perform other functions attributed to processor 80 of IMD 16.

Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 3).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Figure 5:
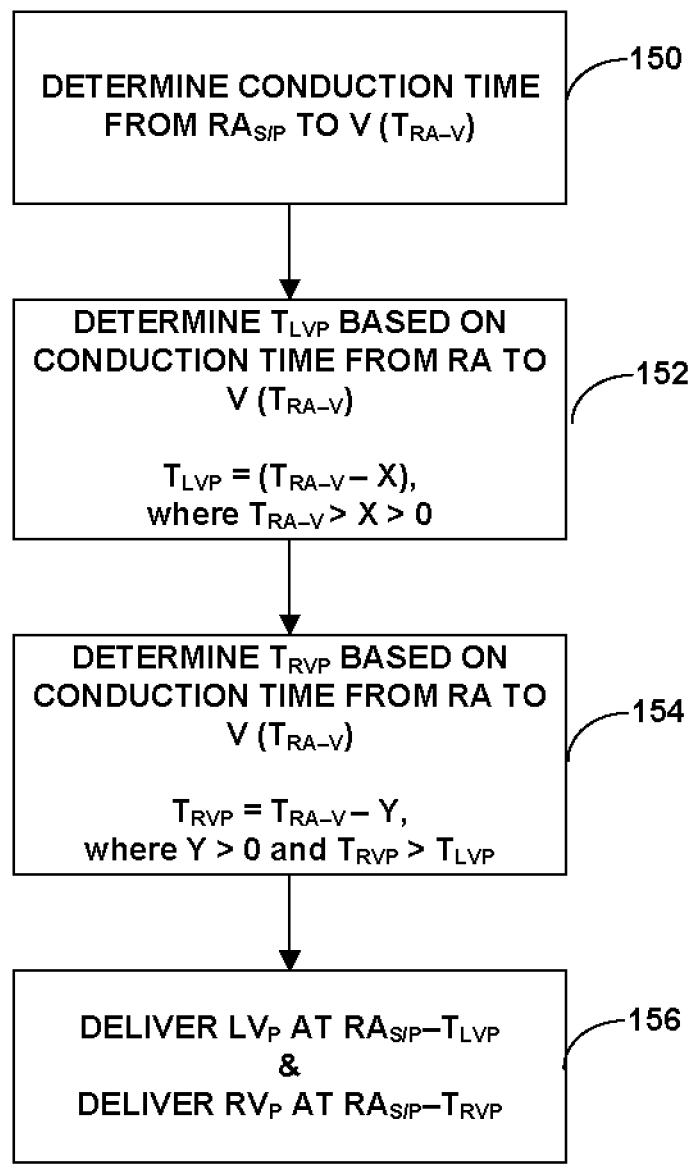
FIGS. 5 and 6 are flow diagrams of example techniques for determining when to deliver pacing therapy to left and right ventricles of a heart.
Figure 6:
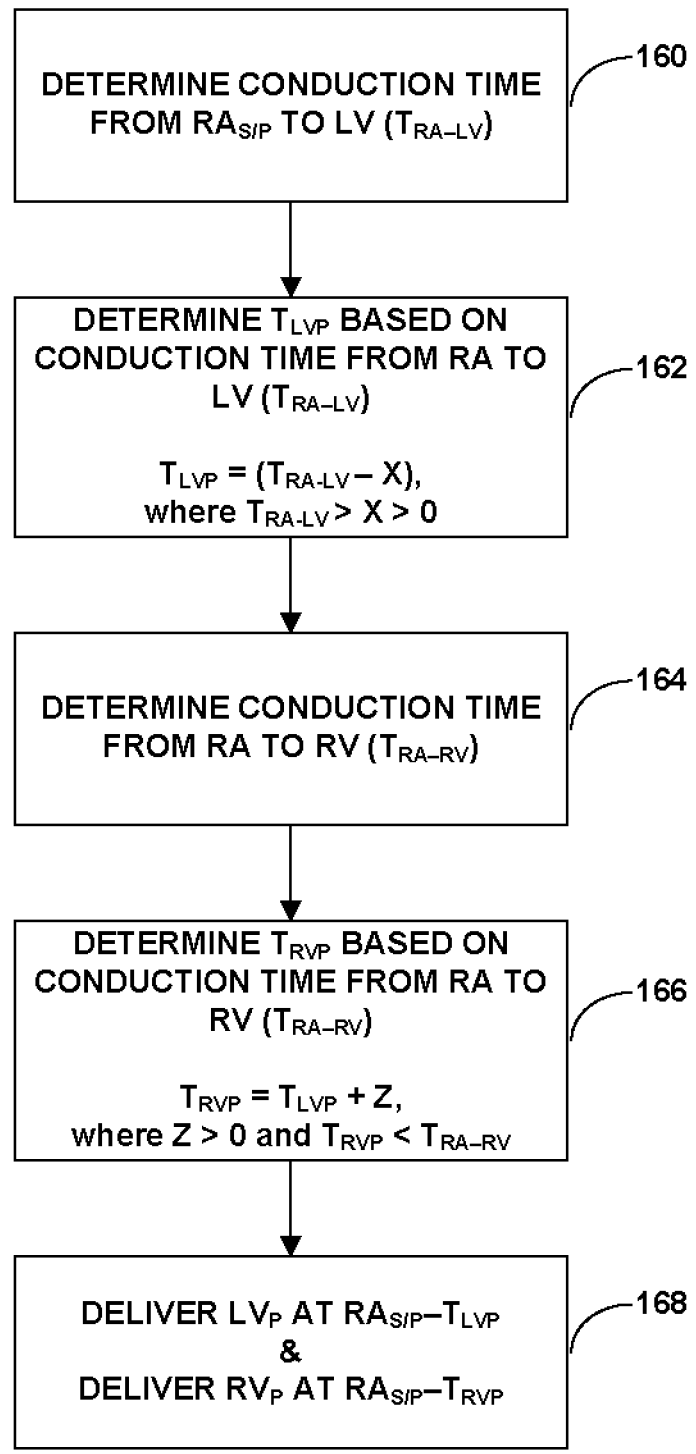
Figure 7:
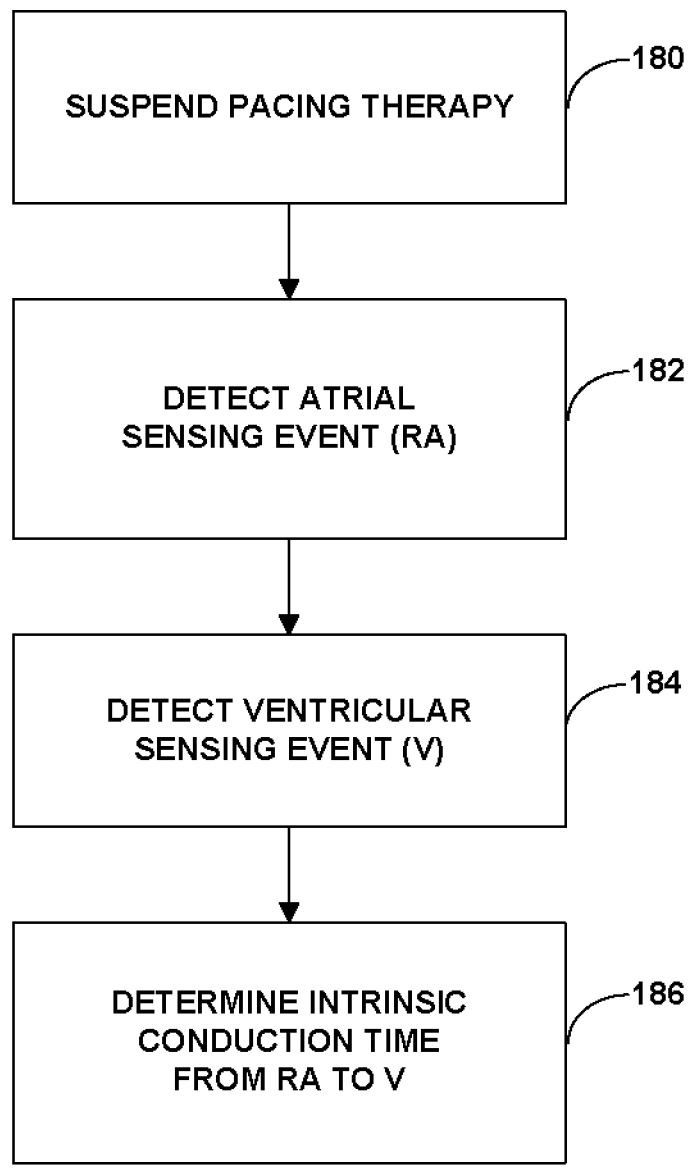
FIG. 7 is a flow diagram of an example technique for determining a time interval between an atrial sensing event and a ventricular sensing event.

Power source 108 delivers operating power to the components of programmer 24. Power source 108 may include a battery and a power generation circuit to produce the operating power. The battery may be a rechargeable or non-rechargeable battery Example techniques that IMD 16 (or another computing device, such as programmer 24) may implement in order to determine when to deliver pacing therapy to left ventricle 32 and right ventricle 28 of patient 14 are described with respect to FIGS. 5-7. FIGS. 5 and 6 describe example techniques for determining a left-ventricular pacing interval ($A_{S/P}$-$LV_P$) and a right-ventricular pacing interval ($A_{S/P}$-$RV_p$) in order to achieve dyssynchronous activation and contraction of left ventricle 32 and right ventricle 28 (FIG. 1). FIG. 7 describes an example technique for determining a time interval between an atrial sensing event and a ventricular sensing event.

FIG. 5 is a flow diagram of an example technique for determining a time interval $T_{A-V}$, determining times $T_{LVP}$ and $T_{RVP}$ for delivering pacing pulses to left ventricle 32 and right ventricle 28 (FIG. 2), respectively, and delivering a left ventricle pacing pulse ($LV_P$) and a right ventricle pacing pulse ($RV_p$) based on the determined times $T_{LVP}$ and $T_{RVP}$. In the technique shown in FIG. 5, processor 80 (FIG. 3) of IMD 16 controls the delivery of a left ventricle pacing pulse ($LV_P$) to left ventricle 32 (FIG. 2) and a right ventricle pacing pulse ($RV_p$) to right ventricle 28 (FIG. 2) relative to an atrial sensing event or pacing event ($A_{S/P}$). While a sensing event or pacing event of right atrium 26 ($RA_{S/P}$) is primarily referred to throughout the description of FIGS. 5 and 6, in other examples, processor 80 can control the delivery of a left ventricle pacing pulse ($LV_P$) to left ventricle 32 and a right ventricle pacing pulse ($RV_p$) to right ventricle 28 based on a left atrium atrial sensing event or pacing event ($LA_{S/P}$). Processor 80 may implement the technique shown in FIG. 5 to determine $A_{S/P}$-$LV_p$ and $A_{S/P}$-$RV_p$ pacing intervals.

In accordance with the technique shown in FIG. 5, processor 80 determines the time interval $T_{RA-V}$ for patient 14, which is the interval of time between an atrial sensing event or atrial pacing event of right atrium 26 (FIG. 2) and a sensing event of a ventricle of heart 12 (150). In some examples, processor 80 detects an atrial sensing event by detecting when an electrical cardiac signal sensed via sensing module 86 is indicative of a P-wave, which can be determined based on the amplitude of the electrical cardiac signal in some examples. The electrical cardiac signal can be sensed via electrodes of lead 22 (FIG. 2) within right atrium 26, as discussed above with respect to FIG. 3, or sensed via electrodes of other leads. In other examples, processor 80 may determine an atrial pacing event by determining that processor 80 is controlling stimulation generator 84 (FIG. 3) to deliver a pacing pulse to electrodes of lead 22 (FIG. 2) within right atrium 26.

Processor may detect a ventricular sensing event by detecting when an electrical cardiac signal sensed via sensing module 86 is indicative of an R-wave. The electrical cardiac signal can be sensed via electrodes of lead 20 (FIG. 2) within left ventricle 32, via electrodes of lead 18 (FIG. 2) within right ventricle 28, and/or via electrodes outside of the ventricles 28, 32. Processor 80 may determine the time interval $T_{RA-V}$ (150), by subtracting the time at which that atrial sensing event or pacing event is detected from the time at which the ventricular sensing event is detected.

In some examples, in order for processor 80 to determine the time interval $T_{RA-V}$ (150), processor 80 may suspend pacing therapy to heart 12, or a portion of heart 12 (e.g., left ventricle 32 and right ventricle 28 (FIG. 2)). Processor 80 may detect an atrial sensing event or atrial pacing event ($A_{S/P}$) of right atrium 26 and a ventricular sensing event of a ventricle of heart 12 while pacing is suspended. In such an example, processor 80 may determine a time interval $T_{RA-V}$ that may be representative of a time between depolarization of right atrium 26 (FIG. 2) (i.e., intrinsic depolarization or depolarization due to a pacing pulse) and intrinsic depolarization of a ventricular chamber of heart 12 (i.e., without pacing the ventricular chamber).

After determining the time interval $T_{RA-V}$ (150), processor 80 may determine a time $T_{LVP}$ for delivering a pacing pulse to left ventricle 32 (FIG. 2) (152). For example, processor 80 may determine a left-ventricular pacing interval $A_{s/p}$-$LV_p$, which is a pacing interval between a subsequently detected atrial sensing event or pacing event and the delivery of a pacing pulse to left ventricle 32. Processor 80 may determine a time $T_{LVP}$ (152) based on the determined time interval $T_{RA-V}$ (150). In accordance with the technique shown in FIG. 5, processor 80 decrements the time interval $T_{RA-V}$ by an amount "X", e.g., based on Equation (2) above, where "X" is less than $T_{RA-V}$ but greater than zero. The variable "X" may be stored in memory 82 (FIG. 3) of IMD 16.

In some examples, IMD 16 can automatically determine a value for "X." In one example, IMD determines a value "X" by sensing a P-wave of heart 12 while IMD 16 is not delivering pacing pulses to the atrial chambers of heart 12. Processor 80 of IMD 16 may then set "X" at a value equal to or greater than the duration of the sensed P-wave. In another example, processor 80 of IMD 16 defines an initial left-ventricular pacing interval ($A_{P/S}$-$LV_P$) based on initial "X" value stored in memory 82 (FIG. 3). Processor 80 then controls stimulation generator 84 to deliver a left ventricle pacing pulse ($LV_P$) based on the initial left-ventricular pacing interval. Processor 80 receives and compares signals generated by sensor 87 (FIG. 3), e.g., to a threshold value or to one or more baseline values sensed while IMD 16 was not delivering pacing therapy to heart 12, and adjusts "X" based on the received signals. In these examples, $T_{LVP}$ times the delivery of a pacing pulse to left ventricle 32 so that the pacing pulse is delivered before the ventricle is intrinsically depolarized via conduction from the AV node.

Processor 80 may also determine a time $T_{RVP}$ for delivering a pacing pulse to right ventricle 28 (FIG. 2) (154). For example, processor 80 may determine a right-ventricular pacing interval $A_{s/p}$-$RV_P$, which is a pacing interval between a subsequently detected atrial sensing event or pacing event and the delivery of a pacing pulse to right ventricle 28. Processor 80 may determine a time $T_{RVP}$ (154) based on the determined time interval $T_{RA-V}$ (150). In accordance with the technique shown in FIG. 5, processor 80 decrements the time interval $T_{RA-V}$ by an amount "Y", e.g., based on Equation (3) above, where "Y" is less than $T_{RA-V}$ but greater than $T_{LVP}$. The variable "Y" may be stored in memory 82 (FIG. 3) of IMD 16.

In some examples, IMD 16 automatically determines a value for "Y." In one example, IMD 16 determines a value "Y" by adding a preset amount of time onto a determined value for "X." For example, processor 80 of IMD 16 may add between approximately 5 milliseconds and approximately 20 milliseconds onto a determined value for "Y." In another example, processor 80 of IMD 16 defines an initial right-ventricular pacing interval ($A_{P/S}$-$RV_P$) based on initial "Y" value stored in memory 82 (FIG. 3). Processor 80 then controls stimulation generator 84 to deliver a right ventricle pacing pulse ($RV_P$) based on the initial right-ventricular pacing interval. Processor 80 receives and compares signals generated by sensor 87 (FIG. 3), e.g., to a threshold value or to one or more baseline values sensed while IMD 16 was not delivering pacing therapy to heart 12, and adjusts "Y" based on the received signals. In these examples, $T_{RVP}$ times the delivery of a pacing pulse to right ventricle 28 so that the pacing pulse is delivered after a pacing pulse is delivered to left ventricle 32.

After determining the time $T_{LVP}$ for delivering a pacing pulse to left ventricle 32 (152) and the time $T_{RVP}$ for delivering a pacing pulse to right ventricle 28, processor 80 may deliver a left ventricle pacing pulse ($LV_P$) and a right ventricle pacing pulse ($RV_P$) (156). Processor 80 may detect an atrial sensing event or an atrial pace of right atrium 26 (FIG. 2). For example, processor 80 may receive an atrial sensing event signal from sensing module 86 (FIG. 2) or control stimulation generator 84 to deliver an atrial pacing pulse to right atrium 26. In some examples, pacing timing and control module 92 (FIG. 4) of processor 80 starts a timer upon the sensing of the atrial event or delivering of an atrial pulse to right atrium 26. Processor 80 controls stimulation generator 84 to deliver a pacing pulse (or a plurality of pacing pulses) to left ventricle 32 after an interval $RA_{S/P}$-$T_{LVP}$, which begins with the atrial sensing event or atrial pacing event of right atrium 26 (156) in the example of FIG. 5. Processor 80 also controls stimulation generator 84 to deliver a pacing pulse (or a plurality of pacing pulses) to right ventricle 28 after an interval $RA_{S/P}$-$T_{RVP}$, which begins with the same atrial sensing event or atrial pacing event of right atrium 26 that begins the interval $RA_{S/P}$-$T_{LVP}$ (156). Timing the delivery of a left ventricle pacing pulse ($LV_P$) and a right ventricle pacing pulse ($RV_P$) in this way may help left ventricle 32 and right ventricle 28 activate and contract out of phase, which may improve the mechanical efficiency (e.g., reduce the preserved ejection fraction) of heart 12 for a person suffering from diastolic heart failure.

FIG. 6 is a flow diagram of an example technique for determining a first time interval $T_{RA-LV}$, determining a time $T_{LVP}$ for delivering a pacing pulse to left ventricle 32 (FIG. 2), determining a second time interval $T_{RA-RV}$, determining a time $T_{RVP}$ for delivering a pacing pulse to right ventricle 28 (FIG. 2), and delivering a left ventricle pacing pulse ($LV_p$) and a right ventricle pacing pulse ($RV_p$) based on the determined times $T_{LVP}$ and $T_{RVP}$. Because the technique of FIG. 6 determines a first time interval $T_{RA-LV}$ from the right atrium to the left ventricle and a second time interval $T_{RA-RV}$ from the right atrium to the right ventricle, the technique of FIG. 6 may be useful for patients in which the intrinsic conduction time from an atrium to the right ventricle differs by a certain amount relative to the intrinsic conduction time from the atrium to the left ventricle when pacing pulses are not being delivered to the ventricles. For example, the technique may determine different intrinsic conduction times between a right atrium and a right ventricle, and a right atrium and a left ventricle, and further determine a right-ventricular pacing interval and a left-ventricular pacing interval based on a respective intrinsic conduction time.

As with the technique of FIG. 5, in the technique shown in FIG. 6, processor 80 (FIG. 3) of IMD 16 controls the delivery of a left ventricle pacing pulse ($LV_p$) to left ventricle 32 (FIG. 2) and a right ventricle pacing pulse ($RV_p$) to right ventricle 28 (FIG. 2) relative to an atrial sensing event or pacing event ($A_{S/P}$)), which is primarily described as being a sensing or a pacing event of right atrium 26. In other examples, the sensing or pacing event can be of left atrium 36. Processor 80 may implement the technique shown in FIG. 6 to determine $A_{S/P}$-$LV_p$ and $A_{S/P}$-$RV_p$ pacing intervals.

In accordance with the technique shown in FIG. 6, processor 80 determines a first time interval $T_{RA-LV}$ for patient 14, which is the interval of time between an atrial sensing event or atrial pacing event of right atrium 26 (FIG. 2) and a sensing event of left ventricle 32 (160). As discussed above with respect to FIG. 5, processor 80 may detect an atrial sensing event by detecting when an electrical cardiac signal sensed via sensing module 86 is indicative of a P-wave, which can be determined based on the amplitude of the electrical cardiac signal or another suitable technique. The electrical cardiac signal can be sensed via electrodes of lead 22 (FIG. 2) within right atrium 26, as discussed above with respect to FIG. 3, or sensed via electrodes of other leads. In other examples, processor 80 may determine an atrial pacing event by determining that processor 80 is controlling stimulation generator 84 (FIG. 3) to deliver a pacing pulse to electrodes of lead 22 (FIG. 2) within right atrium 26.

Processor 80 may detect a ventricular sensing event by detecting when an electrical cardiac signal (e.g., an EGM) sensed via sensing module 86 is indicative of an R-wave. The electrical cardiac signal can be sensed via electrodes of lead 20 (FIG. 2) within left ventricle 32 or by electrodes of another lead. Processor 80 may determine the time interval $T_{RA-LV}$ (160), by subtracting the time at which that atrial sensing event or pacing event is detected from the time at which the ventricular sensing event is detected. In some examples, in order for processor 80 to determine the time interval $T_{RA-LV}$ (160), processor 80 may suspend pacing therapy to heart 12, or a portion of heart 12 (e.g., left ventricle 32 and right ventricle 28 (FIG. 2)). Processor 80 may detect an atrial sensing event or atrial pacing event ($A_{sa}$)) of right atrium 26 and a ventricular sensing event of left ventricle 32 while pacing is suspended. In such an example, processor 80 may determine a conduction time from right atrium 26 to left ventricle 32, i.e., time interval $T_{RA-LV}$, which may be representative of a time between depolarization of right atrium 26 (FIG. 2) (i.e., intrinsic depolarization or depolarization due to a pacing pulse) and intrinsic depolarization of left ventricular 32 (i.e., without pacing the ventricular chamber).

After determining the first time interval $T_{RA-LV}$ (160), processor 80 may determine a time $T_{LVP}$ for delivering a pacing pulse to left ventricle 32 (FIG. 2) (162). For example, processor 80 may determine a left-ventricular pacing interval $A_{s/p}$-$LV_P$, which is a pacing interval between a subsequently detected atrial sensing event or pacing event and the delivery of a pacing pulse to left ventricle 32. Processor 80 may determine a time $T_{LVP}$ (162) based on the determined first time interval $T_{RA-LV}$ (160). In accordance with the technique shown in FIG. 6, processor 80 decrements the time interval $T_{RA-V}$ by an amount "X", e.g., based on Equation (2) above, where "X" is less than $T_{RA-LV}$ but greater than zero. The variable "X" may be stored in memory 82 (FIG. 3) of IMD 16. In some examples, processor 80 automatically determines a value for "X," as discussed above with respect to FIGS. 1 and 5. Thus, in this example, $T_{LVP}$ controls the time at which a pacing pulse is delivered to left ventricle 32 so that the pacing pulse is delivered before the ventricle is intrinsically depolarized via conduction from the AV node.

Processor 80 may also determine a second time interval $T_{RA-RV}$ for patient 14, which is the interval of time between an atrial sensing event or atrial pacing event of right atrium 26 (FIG. 2) and a sensing event of right ventricle 28 (164).

Similar to the process described above by which processor 80 may determine the first time interval $T_{RA-LV}$ (160), processor 80 may detect an atrial sensing event by detecting a P-wave of an electrical cardiac signal sensed with sensing module 86 of IMD 16. In some examples, processor 80 determines an atrial pacing event by determining that processor 80 is controlling stimulation generator 84 (FIG. 3) to deliver a pacing pulse to electrodes of lead 22 (FIG. 2) within right atrium 26. Processor may detect a ventricular sensing event by detecting an R-wave of an electrical cardiac signal sensed via sensing module 86 of IMD 16. Processor 80 may determine the time interval $T_{RA-RV}$ (164), by subtracting the time at which the right atrial sensing event or pacing event is detected from the time at which the right ventricular sensing event is detected.

In some examples, processor 80 may determine the second time interval $T_{RA-RV}$ based on signals sensed by sensing module 86 (FIG. 3) during the same cardiac cycle(s) during which sensing module 86 senses signals for determining first time interval $T_{RA-LV}$. For example, as described with the technique of FIG. 5, processor 80 may suspend pacing therapy to heart 12, or a portion of heart 12 (e.g., left ventricle 32 and right ventricle 28 (FIG. 2)). Processor 80 may detect an atrial sensing event or atrial pacing event ($A_{S/P}$) of right atrium 26 and a ventricular sensing event of right ventricle 28 while pacing is suspended. In such an example, processor 80 may determine a second time interval $T_{RA-RV}$ that may be representative of a conduction time from right atrium 26 to right ventricle 28, which is representative of the time between depolarization of right atrium 26 (FIG. 2) (i.e., intrinsic depolarization or depolarization due to a pacing pulse) and intrinsic depolarization of right ventricular 28 (i.e., without pacing the ventricular chamber).

After determining the second time interval $T_{RA-RV}$ (164), processor 80 determines a time $T_{RVP}$ for delivering a pacing pulse to right ventricle 28 (FIG. 2) (166). For example, processor 80 may determine a right-ventricular pacing interval $A_{s/p}$-$RV_P$, which is a pacing interval between a subsequently detected atrial sensing event or pacing event and the delivery of a pacing pulse to right ventricle 28. Processor 80 may determine a time $T_{RVP}$ based on the determined time $T_{LVP}$ for delivering a pacing pulse to left ventricle 32 (166). In accordance with the technique shown in FIG. 6, processor 80 increments the time $T_{LVP}$ by an amount "Z", e.g., based on Equation (4) above, where "Z" is greater than zero and $T_{LVP}$+Z is less than the second time interval $T_{RA-RV}$. The variable "Z" may be stored in memory 82 (FIG. 3) of IMD 16. In some examples, processor 80 of IMD 16 automatically determines a value for "Z.". Thus, in this example, $T_{RVP}$ controls the time at which a pacing pulse is delivered to right ventricle 28 so that the pacing pulse is delivered after a pacing pulse is delivered to left ventricle 32 but before the right ventricle is intrinsically depolarized via conduction from the AV node.

After determining the time $T_{LVP}$ for delivering a pacing pulse to left ventricle 32 (162) and the time $T_{RVP}$ for delivering a pacing pulse to right ventricle 28 (166), processor 80 may deliver a left ventricle pacing pulse ($LV_P$) and a right ventricle pacing pulse ($RV_P$) (168). Processor 80 may detect an atrial sensing event or an atrial pace of right atrium 26 (FIG. 2). For example, processor 80 may receive an atrial sensing event signal from sensing module 86 (FIG. 2) or control stimulation generator 84 to deliver an atrial pace to right atrium 26. In some examples, pacing timing and control module 92 (FIG. 4) of processor 80 starts a timer upon the sensing of the atrial event or delivering of an atrial pulse to right atrium 26. Processor 80 controls stimulation generator 84 to deliver a pacing pulse (or a plurality of pacing pulses) to left ventricle 32 after an interval $RA_{S/P}$-$T_{LVP}$, which begins with the atrial sensing event or atrial pacing event of right atrium 26 (168) in the example of FIG. 6. Processor 80 also controls stimulation generator 84 to deliver a pacing pulse (or a plurality of pacing pulses) to right ventricle 28 after an interval $RA_{S/P}$-$T_{RVP}$, which begins with the same atrial sensing event or atrial pacing event of right atrium 26 that begins the interval $RA_{S/P}$-$T_{LVP}$ (168). Timing the delivery of a left ventricle pacing pulse ($LV_P$) and a right ventricle pacing pulse ($RV_P$) in this way may help left ventricle 32 and right ventricle 28 to activate and contract out of phase, which may improve the mechanical efficiency (e.g., reduce the preserved ejection fraction) of heart 12 for a person suffering from diastolic heart failure.

As previously indicated, in some examples, processor 80 may suspend pacing therapy to heart 12 to determine a time interval $T_{A-V}$ from which processor 80 may further determine pacing times $T_{LVP}$ and $T_{RVP}$. FIG. 7 is a flow diagram of an example technique for determining a time interval $T_{RA-V}$, which is a time interval between an atrial sensing event of right atrium 26 (FIG. 2) and a ventricular sensing event of a ventricle of heart 12. In accordance with the technique of FIG. 7, processor 80 control stimulation generator 84 (FIG. 3) to suspend the delivery of pacing pulses to heart 12 (180). After suspending the pacing pulses, processor 80 may detect an atrial sensing event in right atrium 26 (FIG. 2) based on signals sensed by sensing module 86 (FIG. 3) (182). For example, processor 80 may detect an atrial sensing event by sensing a P-wave (e.g., of a sensed EGM) via electrodes of lead 22 (FIG. 2) within right atrium 26 based on signals generated by sensing module 86 of IMD 16 or electrodes of one or both of leads 18, 20.

After suspending the pacing pulses, processor 80 may also detect a ventricular sensing event ($V_S$) in a ventricle of heart 12 based on signals sensed by sensing module 86 (FIG. 3) (184). Processor 80 may detect a ventricular sensing event by sensing an R-wave (e.g., of a sensed EGM) via electrodes of lead 18 (FIG. 2) within right ventricle 28 based on signals generated by sensing module 86 of IMD 16. In other examples, processor 80 detects a ventricular sensing event by sensing an R-wave (e.g., of a sensed EGM) via electrodes of lead 20 (FIG. 2) within left ventricle 32 based on signals generated by sensing module 86 of IMD 16.

Processor 80 may determine an intrinsic conduction time $T_{RA-V}$ from right atrium 26 to a ventricle of heart 12 based on the detected atrial sensing event of right atrium 26 and the detected ventricular sensing (186). For example, processor 80 may determine the time interval $T_{RA-V}$ (186) by subtracting the time at which that atrial sensing event is detected from the time at which the ventricular sensing event is detected.

In some examples, processor 80 may suspend pacing pulses to heart 12 for one cardiac cycle and determine an intrinsic conduction time $T_{RA-V}$ from right atrium 26 to a ventricle of heart 12 based on an atrial sensing event of right atrium 26 and a ventricular sensing of heart 12 detected during the one cardiac cycle. In other examples, processor 80 may suspend pacing pulses to heart 12 for a plurality of cardiac cycles. In accordance with this example, processor may detect a plurality of atrial sensing event in right atrium 26 (FIG. 2) and a plurality of ventricular sensing events of heart 12 based on signals sensed by sensing module 86 (FIG. 3) during each of the plurality of cardiac cycles. Processor 80 may determine a plurality of intrinsic conduction times $T_{RA-V}$ based on the plurality of detected sensing events of right atrium 26 and the plurality of detected sensing events of a ventricle of heart 12. For example, processor 80 may determine a time interval $T_{RA-V}$ for each cardiac cycle by subtracting the time at which the atrial sensing event is detected for that cardiac cycle from the time at which the ventricular sensing event is detected for that cardiac cycle. As described above, processor 80 may also select one of the plurality of determined time intervals $T_{RA-V}$ (e.g., the smallest, largest, medium, and/or mode time interval $T_{RA-V}$) or determine a composite time interval $T_{RA-V}$ (e.g., a mean time interval $T_{RA-V}$) for subsequently determining the $T_{LVP}$ and $T_{RVP}$ pacing times.

Figure 8B:
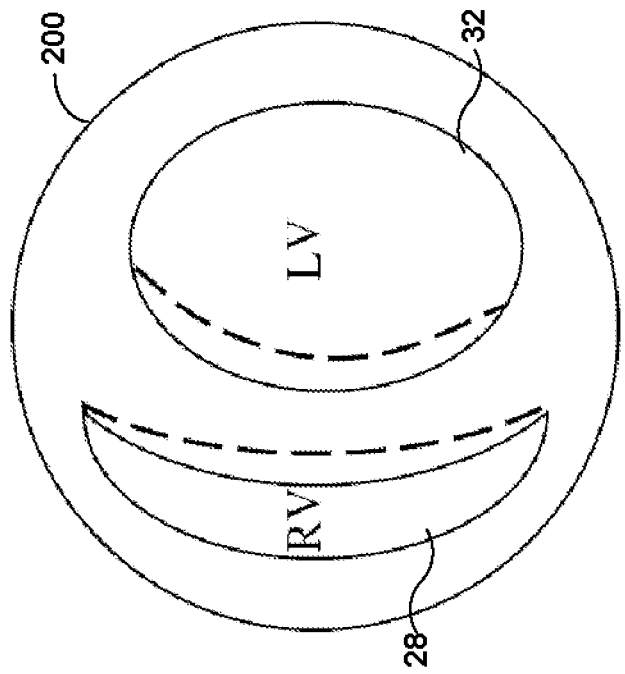
FIGS. 8A and 8B are conceptual diagrams illustrating example left and right heart ventricles during dyssynchronous contraction.
Figure 8A:
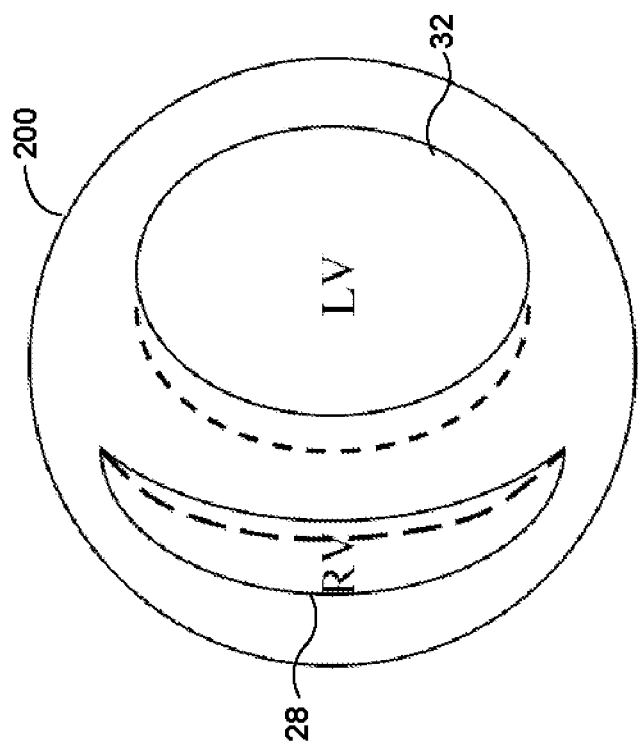

As previously indicated, in some examples, processor 80 may control stimulation generator 84 to deliver a left ventricle pacing pulse ($LV_P$) and a right ventricle pacing pulse ($RV_P$) that results in dyssynchronous activation and contraction of left ventricle 32 and right ventricle 28 (FIG. 2). FIGS. 8A and 8B are conceptual diagrams illustrating an example of left ventricle 32 and right ventricles 28 during such dyssynchronous activation and contraction.

As seen in FIGS. 8A and 8B, left ventricle 32 and right ventricle 28 are enclosed within pericardium 200, which is a sac that surrounds heart 12 (FIG. 1). In a normal electrical activation sequence, left ventricle 32 contacts (e.g., shrinks) and relaxes (e.g., expands) in synchrony with right ventricle 28 within the constrained space of pericardium 200. However, for some patients, such as patients with diastolic heart failure, left ventricle 32 and/or right ventricle 28 cannot fully relax within pericardium 200. For example, for patients with left ventricle hypertrophy, left ventricle 32 may increase in bulk due to the thickening of the muscle fibers of the ventricle. As a result, left ventricle 32 and right ventricle 28 may compete for space within pericardium 200 when the two ventricles attempt to relax in synchrony. For example, for some patients, right ventricle 28 may displace a portion of left ventricle 32 at the end of diastolic filling reducing the amount of blood that enters into left ventricle 32 during diastole as compared to when the ventricle fully relaxes.

Processor 80 may control stimulation generator 84 (FIG. 3) to deliver a left ventricle pacing pulse ($LV_P$) and a right ventricle pacing pulse ($RV_P$), e.g., in accordance with the one of the techniques shown in FIGS. 5 and 6, which may help alleviate diastolic heart failure by pacing left ventricle 32 and right ventricle 28 so that the ventricles contract and relax out of phase (i.e., the minimum diastolic pressure of left ventricle 32 during a cardiac cycle is shifted relative to the minimum diastolic pressure of right ventricle 28 during the same cardiac cycle). As illustrated in FIG. 8A, during pacing therapy from IMD 16, right ventricle 28 may contract within pericardium 200 (e.g., to the dashed line within right ventricle 28 indicated on FIG. 8A) while left ventricle 32 relaxes and expands within pericardium 200 (e.g., to the dashed line extending from left ventricle 32 on FIG. 8A). Conversely, as illustrated in FIG. 8B, right ventricle 28 may expand and relax within pericardium 200 (e.g., to the dashed line extending from right ventricle 28 on FIG. 8B) while left ventricle 32 contracts within pericardium 200 (e.g., to the dashed line in left ventricle 32 indicated on FIG. 8B) during pacing from IMD 16. In this way, right ventricle 28 and left ventricle 32 may expand and contract out of phase (i.e., at different times) so the two ventricles do not compete for space within pericardium 200, or at least decrease the extent to which the ventricles compete for space within pericardium 200. By decreasing the extent to which right ventricle 28 and left ventricle 32 compete for space within pericardium 200, each ventricle may more fully relax within pericardium 200, which may improve the mechanical efficiency of heart 12 (FIG. 1).

Figure 9:
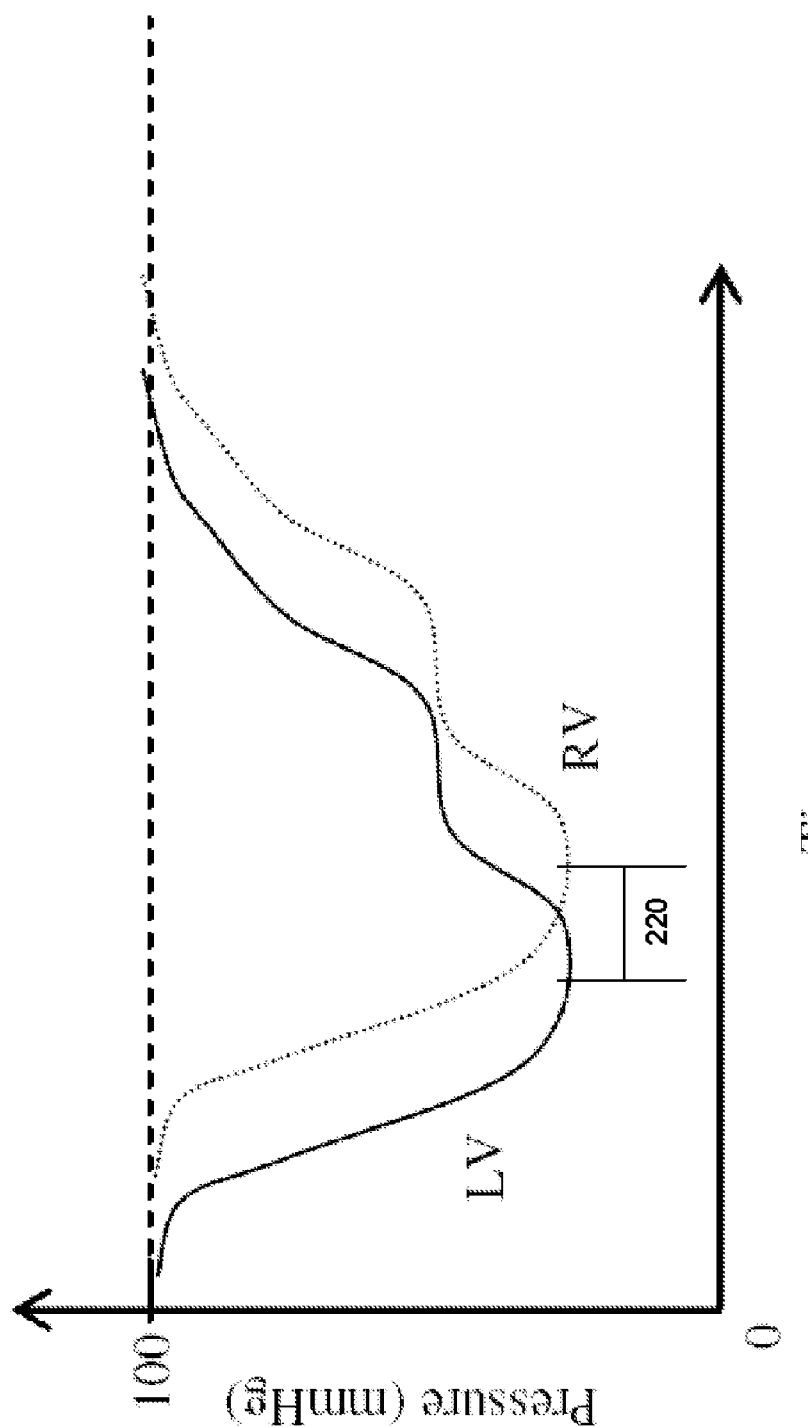
FIG. 9 is a plot of example ventricular pressures versus time for left and right heart ventricles during a cardiac cycle.

FIG. 9 is a plot of example ventricular pressures versus time for left ventricle 32 and right ventricle 28 during a cardiac cycle in which processor 80 is controlling stimulation generator 84 to deliver a left ventricle pacing pulse ($LV_P$) and a right ventricle pacing pulse ($RV_P$) according to the techniques described herein. As seen in FIG. 9, the pressure of left ventricle 32 is out of phase with right ventricle 28, indicating dyssynchrony between left ventricle 32 and right ventricle 28. In particular, the minimum diastolic pressure of left ventricle 32 is out of phase with the minimum diastolic pressure of right ventricle 28 by a time 220. Time 220 may vary depending on the specific patient and the specific pacing intervals used for determining when to deliver a left ventricle pacing pulse ($LV_P$) and a right ventricle pacing pulse ($RV_P$). However, in some examples, time 220 may range from approximately 5 milliseconds to approximately 100 milliseconds. Other times are contemplated.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure. The computer-readable medium may be non-transitory.

Various examples have been described. These and other examples are within the scope of the following claims.

The invention claimed is:

1. A method comprising:
   determining, with a processor, a time interval between at least one of an atrial sensing event or an atrial pacing event of an atrial chamber of a heart and a ventricular sensing event of a ventricular chamber of the heart;
   determining, with the processor, a left-ventricular pacing interval based on the time interval, wherein the left-ventricular pacing interval is less than the time interval; and
   determining, with the processor, a right-ventricular pacing interval based on the time interval, wherein the right-ventricular pacing interval is greater than the left-ventricular pacing interval and less than the time interval.

2. The method of claim 1, wherein determining the right-ventricular pacing interval comprises determining the right-ventricular pacing interval based on the left-ventricular pacing interval.

3. The method of claim 1, wherein determining the time interval between at least one of an atrial sensing event or an atrial pacing event of an atrial chamber of a heart and a ventricular sensing event of a ventricular chamber of the heart comprises determining a first time interval between at least one of the atrial sensing event or the atrial pacing event of a right atrial chamber of the heart and a first ventricular sensing event of a left ventricular chamber of the heart, and a second time interval between at least one of the atrial sensing event or the atrial pacing event of the right atrial chamber of the heart and a second ventricular sensing event of a right ventricular chamber of the heart, wherein determining the left-ventricular pacing interval based on the time interval comprises determining the left-ventricular pacing interval based on the first time interval, wherein the left-ventricular pacing interval is less than the first time interval, and wherein determining the right-ventricular pacing interval based on the time interval comprises determining the right-ventricular pacing interval based on the second time interval, wherein the right-ventricular pacing interval is greater than the left-ventricular pacing interval and less than the second time interval.

4. The method of claim 3, wherein the left-ventricular pacing interval is a pacing interval from a detection of at least one of the atrial sensing event or the atrial pacing event of a right atrial chamber of the heart to a delivery of a left-ventricular pacing pulse to a left ventricular chamber of the heart, the right-ventricular pacing interval is a pacing interval from a detection of at least one of the atrial sensing event or the atrial pacing event of the right atrial chamber of the heart to a delivery of a right-ventricular pacing pulse to a right ventricular chamber of the heart, and
   wherein determining the left-ventricular pacing interval and determining the right-ventricular pacing interval comprises determining the left-ventricular pacing interval and determining the right-ventricular pacing interval to maximize a time delay between the delivery of the left-ventricular pacing pulse and the delivery of the right-ventricular pacing pulse.

5. The method of claim 1, wherein determining the time interval comprises:
   detecting at a first time at least one of the atrial sensing event or the atrial pacing event of the right atrial chamber of the heart;
   detecting at a second time the ventricular sensing event of the ventricular chamber of the heart; and
   determining the time interval based on the first time and the second time.

6. The method of claim 5, wherein detecting the ventricular sensing event comprises detecting an R-wave of an electrical cardiac signal sensed by an implantable medical device.

7. The method of claim 1, wherein determining the time interval comprises:
   suspending, for at least one cardiac cycle, a pacing therapy delivered to the heart by a medical device;
   detecting, while the pacing therapy delivered to the heart is suspended, the atrial sensing event of the atrial chamber of the heart;
   detecting, while the pacing therapy delivered to the heart is suspended, the ventricular sensing event of the ventricular chamber of the heart; and
   determining the time interval based on the detected atrial sensing event and the detected ventricular sensing event.

8. The method of claim 7, wherein the at least one cardiac cycle comprises a plurality of cardiac cycles, detecting the atrial sensing event comprises detecting a plurality of atrial sensing events, detecting the ventricular sensing event comprises detecting a plurality of ventricular sensing events, and wherein determining the time interval comprises determining at least one of a mean, median, smallest, or largest time interval between each detected atrial sensing event of the plurality of detected atrial sensing events and a respective ventricular sensing event of the plurality of detected ventricular sensing events.

9. The method of claim 1, further comprising:
detecting of at least one of the atrial sensing event or the atrial pacing event of the right atrial chamber;
with a medical device, delivering a left-ventricular pacing pulse to a left ventricular chamber of the heart upon expiration of the left-ventricular pacing interval that begins at detection of at least one of the atrial sensing event or the atrial pacing event of the right atrial chamber; and
with the medical device, delivering a right-ventricular pacing pulse to a right ventricular chamber of the heart upon expiration of the right-ventricular pacing interval that begins at detection of at least one of the atrial sensing event or the atrial pacing event of the right atrial chamber.

10. A system comprising:
a stimulation generator that is configured to deliver a left-ventricular pacing pulse to a left ventricular chamber of a heart, and to deliver a right-ventricular pacing pulse to a right ventricular chamber of the heart; and
a processor that is configured to detect at least one of an atrial sensing event or an atrial pacing event of an atrial chamber of the heart, wherein the processor is configured to determine a time interval between at least one of the atrial sensing event or the atrial pacing event of the atrial chamber of the heart and a ventricular sensing event of the ventricular chamber of the heart during a first cardiac cycle, determine a left-ventricular pacing interval based on the time interval, wherein the left-ventricular pacing interval is less than the time interval, and determine a right-ventricular pacing interval based on the time interval, wherein the right-ventricular pacing interval is greater than the left-ventricular pacing interval and less than the time interval, and wherein the processor is configured to control the stimulation generator to deliver the left-ventricular pacing pulse upon expiration of the left-ventricular pacing interval that begins at detection of at least one of the atrial sensing event or the atrial pacing event of the atrial chamber during a second cardiac cycle, and deliver the right-ventricular pacing pulse upon expiration of the right-ventricular pacing interval that begins at detection of at least one of the atrial sensing event or the atrial pacing event of the atrial chamber during the second cardiac cycle.

11. The system of claim 10, wherein the processor is further configured to determine the right-ventricular pacing interval based on the left-ventricular pacing interval.

12. The system of claim 10, further comprising a sensing module, wherein the processor is configured to control the sensing module to sense the atrial sensing event.

13. The system of claim 10, wherein the processor is configured to control the stimulation generator to deliver an atrial pacing pacing pulse, and wherein the processor is configured to detect the atrial pacing event at least by controlling the stimulation generator to deliver the atrial pacing pacing pulse.

14. The system of claim 10, wherein the at least one of the atrial sensing event or the atrial pacing event of the atrial chamber of the heart comprises at least one of the atrial sensing event or the atrial pacing event of a right atrial chamber of the heart.

15. The system of claim 10, wherein the processor is further configured to determine a first time interval between at least one of the atrial sensing event or the atrial pacing event of the atrial chamber of the heart and a first ventricular sensing event of the left ventricular chamber of the heart during the first cardiac cycle, determine a second time interval between at least one of the atrial sensing event or the atrial pacing event of the atrial chamber of the heart and a second ventricular sensing event of the right ventricular chamber of the heart during the first cardiac cycle, determine the left-ventricular pacing interval based on the first time interval, wherein the left-ventricular pacing interval is less than the first time interval, and determine the right-ventricular pacing interval based on the second time interval, wherein the right-ventricular pacing interval is greater than the left-ventricular pacing interval and less than the second time interval.

16. The system of claim 15, wherein the processor is configured to determine the left-ventricular pacing interval and to determine the right-ventricular pacing interval to maximize a time delay between the delivery of the left-ventricular pacing pulse and the delivery of the right-ventricular pacing pulse.

17. The system of claim 10, wherein the processor is configured to detect at a first time the at least one of the atrial sensing event or the atrial pacing event of a right atrial chamber of the heart, detect at a second time the ventricular sensing event of the ventricular chamber of the heart, and determine the time interval based on the first time and the second time.

18. The system of claim 10, further comprising a sensing module that monitors an electrical cardiac signal of the ventricular chamber via at least one electrode, wherein the processor detects the ventricular sensing event by at least detecting an R-wave of the electrical cardiac signal.

19. The system of claim 10, wherein the processor is configured to suspend, for at least one cardiac cycle, a pacing therapy delivered to the heart by the stimulation generator, detect, while the pacing therapy delivered to the heart is suspended, the atrial sensing event of the atrial chamber of the heart, detect, while the pacing therapy delivered to the heart is suspended, the ventricular sensing event of the ventricular chamber of the heart, and determine the time interval based on the detected atrial sensing event and the detected ventricular sensing event.

20. The system of claim 19, wherein the at least one cardiac cycle comprises a plurality of cardiac cycles, the processor is configured to detect a plurality of atrial sensing events, the processor is configured to detect a plurality of ventricular sensing events, and wherein the processor is further configured to determine the time interval by at least determining at least one of a mean, a greatest, or a smallest time interval between each detected atrial sensing event of the plurality of detected atrial sensing events and a respective ventricular sensing event of the plurality of detected ventricular sensing events.

21. A system comprising:
means for determining a time interval between at least one of an atrial sensing event or an atrial pacing event of an atrial chamber of a heart and a ventricular sensing event of a ventricular chamber of the heart;
means for determining a left-ventricular pacing interval based on the time interval, wherein the left-ventricular pacing interval is less than the time interval; and means for determining a right-ventricular pacing interval based on the time interval, wherein the right-ventricular pacing interval is greater than the left-ventricular pacing interval and less than the time interval.

22. The system of claim 21, wherein the means for determining the right-ventricular pacing interval comprises means for determining the right-ventricular pacing interval based on the left-ventricular pacing interval.

23. The system of claim 21, wherein the means for determining the time interval between at least one of an atrial sensing event or an atrial pacing event of an atrial chamber of a heart and a ventricular sensing event of a ventricular chamber of the heart comprises means for determining a first time interval between at least one of the atrial sensing event or the atrial pacing event of a right atrial chamber of the heart and a first ventricular sensing event of a left ventricular chamber of the heart, and means for determining a second time interval between at least one of the atrial sensing event or the atrial pacing event of the right atrial chamber of the heart and a second ventricular sensing event of a right ventricular chamber of the heart, wherein the means for determining the left-ventricular pacing interval based on the time interval comprises means for determining the left-ventricular pacing interval based on the first time interval, wherein the left-ventricular pacing interval is less than the first time interval, and wherein the means for determining the right-ventricular pacing interval based on the time interval comprises means for determining the right-ventricular pacing interval based on the second time interval, wherein the right-ventricular pacing interval is greater than the left-ventricular pacing interval and less than the second time interval.

24. The system of claim 23, wherein the left-ventricular pacing interval is a pacing interval from a detection of at least one of the atrial sensing event or the atrial pacing event of a right atrial chamber to a delivery of a left-ventricular pacing pulse to a left ventricular chamber of the heart, the right-ventricular pacing interval is a pacing interval from a detection of at least one of the atrial sensing event or the atrial pacing event of the right atrial chamber to the delivery of a right-ventricular pacing pulse to a right ventricular chamber of the heart, and wherein the means for determining the left-ventricular pacing interval and the means for determining the right-ventricular pacing interval determine the left-ventricular pacing interval and the right-ventricular pacing interval, respectively, to maximize a time delay between the delivery of the left-ventricular pacing pulse and the delivery of the right-ventricular pacing pulse.

25. The system of claim 21, wherein means for determining the time interval comprises:
means for detecting at a first time at least one of the atrial sensing event or the atrial pacing event of the right atrial chamber of the heart;
means for detecting at a second time the ventricular sensing event of the ventricular chamber of the heart; and
means for determining the time interval based on the first time and the second time.

26. The system of claim 21, further comprising:
means for detecting of at least one of the atrial sensing event or the atrial pacing event of a right atrial chamber of the heart;
means for delivering a left-ventricular pacing pulse to a left ventricular chamber of the heart upon expiration of the left-ventricular pacing interval that begins at detection of at least one of the atrial sensing event or the atrial pacing event of the right atrial chamber; and
means for delivering a right-ventricular pacing pulse to a right ventricular chamber of the heart upon expiration of the right-ventricular pacing interval that begins at detection of at least one of the atrial sensing event or the atrial pacing event of the right atrial chamber.

27. A non-transitory computer-readable storage medium comprising instructions that cause a programmable processor to:
determine a time interval between at least one of an atrial sensing event or an atrial pacing event of an atrial chamber of a heart and a ventricular sensing event of a ventricular chamber of the heart;
determine a left-ventricular pacing interval based on the time interval, wherein the left-ventricular pacing interval is less than the time interval; and
determine a right-ventricular pacing interval based on the time interval, wherein the right-ventricular pacing interval is greater than the left-ventricular pacing interval and less than the time interval.

28. The computer-readable medium of claim 27, wherein the instructions that cause the programmable processor to determine the time interval between at least one of an atrial sensing event or an atrial pacing event of an atrial chamber of a heart and a ventricular sensing event of a ventricular chamber of the heart comprise instructions that cause the programmable processor to determine a first time interval between at least one of the atrial sensing event or the atrial pacing event of a right atrial chamber of the heart and a first ventricular sensing event of a left ventricular chamber of the heart, and to determine a second time interval between at least one of the atrial sensing event or the atrial pacing event of the right atrial chamber of the heart and a second ventricular sensing event of a right ventricular chamber of the heart, wherein the instructions that cause the programmable processor to determine the left-ventricular pacing interval based on the time interval comprise the instructions that cause the programmable processor to determine the left-ventricular pacing interval based on the first time interval, wherein the left-ventricular pacing interval is less than the first time interval, and wherein the instructions that cause the programmable processor to determine the right-ventricular pacing interval based on the time interval comprise the instructions that cause the programmable processor to determine the right-ventricular pacing interval based on the second time interval, wherein the right-ventricular pacing interval is greater than the left-ventricular pacing interval and less than the second time interval.

29. The computer-readable medium of claim 28, wherein the left-ventricular pacing interval is a pacing interval from a detection of at least one of the atrial sensing event or the atrial pacing event of the right atrial chamber to a delivery of a left-ventricular pacing pulse to a left ventricular chamber of the heart, the right-ventricular pacing interval is a pacing interval from a detection of at least one of the atrial sensing event or the atrial pacing event of the right atrial chamber to a delivery of a right-ventricular pacing pulse to a right ventricular chamber of the heart, and wherein the instructions that cause the programmable processor to determine the left-ventricular pacing interval and to determine the right-ventricular pacing interval comprise instructions that cause the programmable processor to determine the left-ventricular pacing interval and to determine the right-ventricular pacing interval to maximize a time delay between the delivery of the left-ventricular pacing pulse and the delivery of the right-ventricular pacing pulse.

30. The computer-readable medium of claim 27, wherein the instructions that cause the programmable processor to determine the time interval comprise instructions that cause the programmable processor to: suspend, for at least one cardiac cycle, a pacing therapy delivered to the heart;

detect, while the pacing therapy delivered to the heart is suspended, the atrial sensing event of the atrial chamber of the heart;

detect, while the pacing therapy delivered to the heart is suspended, the ventricular sensing event of the ventricular chamber of the heart; and determine the time interval based on the detected atrial sensing event and the detected ventricular sensing event.

31. The computer-readable medium of claim 27, further comprising instructions that cause the programmable processor to:

detect of at least one of the atrial sensing event or the atrial pacing event of a right atrial chamber;

control a stimulation generator to deliver a left-ventricular pacing pulse to a left ventricular chamber of the heart upon expiration of the left-ventricular pacing interval that begins at detection of at least one of the atrial sensing event or the atrial pacing event of the right atrial chamber; and control the stimulation generator to deliver a right-ventricular pacing pulse to a right ventricular chamber of the heart upon expiration of the right-ventricular pacing interval that begins at detection of at least one of the atrial sensing event or the atrial pacing event of the right atrial chamber.

\* \* \* \* \*